United States Patent
Yuan et al.

(10) Patent No.: US 12,277,100 B2
(45) Date of Patent: Apr. 15, 2025

(54) MAINTAINING USER PRIVACY OF PERSONAL, MEDICAL, AND HEALTH CARE RELATED INFORMATION IN RECOMMENDATION SYSTEMS

(71) Applicant: Life Spectacular, Inc., San Francisco, CA (US)

(72) Inventors: Zaoshi Amy Yuan, San Francisco, CA (US); Ming S. Zhao, San Francisco, CA (US)

(73) Assignee: Life Spectacular, Inc., San Francisco, CA (US)

( * ) Notice: Subject to any disclaimer, the term of this patent is extended or adjusted under 35 U.S.C. 154(b) by 190 days.

(21) Appl. No.: 17/700,308

(22) Filed: Mar. 21, 2022

(65) Prior Publication Data

US 2022/0253418 A1 Aug. 11, 2022

Related U.S. Application Data

(63) Continuation-in-part of application No. 17/014,161, filed on Sep. 8, 2020, now Pat. No. 11,328,338.

(60) Provisional application No. 62/899,433, filed on Sep. 12, 2019.

(51) Int. Cl.
| | |
|---|---|
| *G06F 16/22* | (2019.01) |
| *G06F 16/2457* | (2019.01) |
| *G06F 21/62* | (2013.01) |
| *G16H 20/10* | (2018.01) |

(52) U.S. Cl.
CPC .... *G06F 16/2237* (2019.01); *G06F 16/24575* (2019.01); *G06F 16/24578* (2019.01); *G06F 21/6245* (2013.01); *G16H 20/10* (2018.01)

(58) Field of Classification Search
CPC ........... G06F 16/2237; G06F 16/24575; G06F 16/24578; G06F 21/6245; G16H 20/10
USPC ........................................................ 705/2-3
See application file for complete search history.

(56) References Cited

U.S. PATENT DOCUMENTS

| | | | |
|---|---|---|---|
| 7,349,857 | B2 | 3/2008 | Manzo |
| 7,597,247 | B2 | 10/2009 | Helmin et al. |
| 7,809,601 | B2 | 10/2010 | Shaya et al. |
| 8,388,532 | B2 | 3/2013 | Morgan |
| 8,478,009 | B2 | 7/2013 | Wei |
| 9,757,387 | B2 | 9/2017 | Karandikar |
| 9,789,295 | B2 | 10/2017 | Zhou |

(Continued)

OTHER PUBLICATIONS

Iwabuchi, R., Nakajima, Y., Honma, H., Aoshima, H., Kobayashi, A. Akiba, T., Masuyama, S., "Proposal of Recommender System Based on user evaluation and cosmetic ingredients" (Aug. 2017) In: 2017 International Conference on Advanced Infomatics, Concepts, Theory, and Applications 6 pgs.

*Primary Examiner* — Michael Tomaszewski
(74) *Attorney, Agent, or Firm* — Brownstein Hyatt Farber Schreck, LLP

(57) ABSTRACT

Systems and methods for providing recommendations to users while maintaining privacy and information security for those users. In particular, user demographic information and/or geographic/environmental information can be represented as hashes, or fingerprints, which in turn can define a dimension of a recommendation matrix having another dimension defined by attributes of products, services, routines, and so on that may be associated with recommendations to the user. The values of the recommendation matrix can correspond to normalized customer review data and/or other data.

16 Claims, 10 Drawing Sheets

(56) References Cited

U.S. PATENT DOCUMENTS

| | | | |
|---|---|---|---|
| 10,366,793 B2 | 7/2019 | Apte et al. | |
| 10,546,658 B2 | 1/2020 | Salvi et al. | |
| 11,145,412 B2 | 10/2021 | Conway | |
| 11,175,790 B2 | 11/2021 | Mani et al. | |
| 11,328,338 B1 | 5/2022 | Yuan et al. | |
| 11,748,421 B2 * | 9/2023 | Ludwinski | A45D 44/005 706/11 |
| 2002/0035486 A1 | 3/2002 | Huyn et al. | |
| 2002/0038310 A1 | 3/2002 | Reitberg | |
| 2004/0202685 A1 * | 10/2004 | Manzo | C09C 1/62 702/19 |
| 2006/0229912 A1 * | 10/2006 | Negishi | G06Q 30/00 705/2 |
| 2006/0265244 A1 * | 11/2006 | Baumann | A61B 5/441 424/59 |
| 2007/0112585 A1 | 5/2007 | Breiter et al. | |
| 2008/0078828 A1 | 4/2008 | Helmin et al. | |
| 2008/0126129 A1 * | 5/2008 | Manzo | C23C 14/0005 705/2 |
| 2009/0245603 A1 * | 10/2009 | Koruga | A61B 5/444 382/128 |
| 2010/0185064 A1 * | 7/2010 | Bandic | A61B 5/444 600/306 |
| 2011/0105996 A1 | 5/2011 | Mustoe | |
| 2013/0013330 A1 * | 1/2013 | Guerra | G06Q 30/06 705/2 |
| 2014/0018634 A1 | 1/2014 | Baumann | |
| 2014/0072583 A1 | 3/2014 | Ardeleanu | |
| 2014/0188752 A1 | 7/2014 | White et al. | |
| 2014/0214709 A1 | 7/2014 | Greaney | |
| 2014/0295001 A1 * | 10/2014 | Ghorbani | A61K 31/385 424/745 |
| 2014/0344718 A1 | 11/2014 | Rapaport et al. | |
| 2015/0105279 A1 | 4/2015 | Touumazou et al. | |
| 2015/0106123 A1 * | 4/2015 | Amarasingham | G06Q 50/01 705/3 |
| 2017/0035348 A1 * | 2/2017 | Bandic | A61B 5/443 |
| 2018/0374140 A1 * | 12/2018 | Stucki | G06V 40/168 |
| 2019/0065970 A1 | 2/2019 | Bonutti | |
| 2019/0213227 A1 * | 7/2019 | Ludwinski | G06N 20/20 |
| 2019/0213452 A1 * | 7/2019 | Ludwinski | G06V 40/172 |
| 2019/0237194 A1 * | 8/2019 | Salvi | G06N 5/04 |
| 2019/0347296 A1 * | 11/2019 | Parkkinen | G06F 16/90324 |
| 2021/0027897 A1 | 1/2021 | Rasochova et al. | |
| 2021/0035184 A1 | 2/2021 | Lee et al. | |
| 2021/0315512 A1 | 10/2021 | Depfenhart et al. | |
| 2022/0246273 A1 * | 8/2022 | Neumann | G16H 20/60 |

* cited by examiner

600

|  | MATRIX FACTOR X1 | MATRIX FACTOR X2 | MATRIX FACTOR X3 | MATRIX FACTOR X4 |
|---|---|---|---|---|
| MATRIX FACTOR Y1 | A11 | | | |
| MATRIX FACTOR Y2 | | B22 | | |
| MATRIX FACTOR Y3 | | | | D43 |
| MATRIX FACTOR Y4 | | | | |
| MATRIX FACTOR Y5 | | | C35 | |
| | | | | |
| | | | | |
| | | | | |
| | | | | |

*FIG. 6*

MAINTAINING USER PRIVACY OF PERSONAL, MEDICAL, AND HEALTH CARE RELATED INFORMATION IN RECOMMENDATION SYSTEMS

CROSS-REFERENCE TO RELATED APPLICATION(S)

This application is a continuation-in-part of, and claims the benefit under 35 U.S.C. § 120 to U.S. Nonprovisional patent application Ser. No. 17/014,161, filed Sep. 8, 2020, and entitled "Recommendation Matrix," which is a nonprovisional of, and claims the benefit under 35 U.S.C. 119(e) to U.S. Provisional Patent Application No. 62/899,433, filed Sep. 12, 2019, and entitled "Recommendation Matrix," the contents of which are incorporated herein by reference as if fully disclosed herein.

TECHNICAL FIELD

Embodiments described herein relate generally to computing systems, electronic devices, and computing system architectures configured to provide recommendations to one or more users and, in particular, to systems and methods for maintaining user information and data privacy when accessing and leveraging personal care, medical care, nutritional care, and/or health care information when preparing or otherwise generating one or more recommendations to one or more users of a recommendation system.

BACKGROUND

A person can have one or more personal care goals, such as fitness goals, mental and/or physical health goals, medical goals, nutritional goals, and the like. A person may also have one or more personal preferences—which may or may not be directly related to health or well-being—such as preferences regarding outward appearance (e.g., use of cosmetics, hair dyes, body modifications, piercings, tattoos, and so on), products to consume or from which to abstain (e.g., dietary preferences), industries or companies to support or avoid, and so on.

As known to many, personal goals and personal preferences like these and others may be achieved, advanced, or pursued in whole or in part by using—as directed—one or more commercially-available products. Unfortunately, however, it is often challenging, for a person to identify one or more (in-budget) products that meaningfully advance or otherwise accommodate a personal goal or preference without introducing negative side effects and/or without negatively interacting with other products used by that person. As a result, individuals often seek out recommendations and/or expert advice prior to purchasing commercially-available products or services in order to inform purchase decisions.

As known to many, a person may seek out professional advice and/or recommendations from a medical professional, nutritionist, aesthetician, physical therapist, psychiatrist, counselor, or other similar professional. In many cases, however, personal care goals or preferences can be exceptionally private matters, and the person may be too embarrassed, shy, or otherwise hesitant to seek advice of another real, human person—whether in person, via telephone, or via telepresence. Further, in many cases, a person seeking advice from another real human person may not be fully candid when providing information to that person and/or may exaggerate or downplay certain details that, in turn, may cause recommendations given to be, at best, incompletely informed.

In order to avoid seeking advice from real human persons, many people turn to computerized recommendation engines to identify commercially-available products that may help advance or accommodate one or more personal care goals or personal preferences. Conventional consumer product or service recommendation engines typically present to users of those engines a list of consumer products that is sorted and/or filtered based solely on customer reviews or product purchase volume. More sophisticated conventional product recommendation engines provide recommendations by SKU-level collaborative filtering (e.g., user-to-user purchase similarity determinations, item-to-item or product-to-product similarity determinations, and so on) and/or content filtering, based on user profiles or preferences.

However, these and other conventional recommendation engines are often heavily influenced by ad purchasing and are unable to account for survivorship biases introduced by repeated use of those engines. In other words, conventional recommendation engines encourage a cascading feedback effect in which a product that is recommended to users and that is eventually purchased (in part, as a result of the recommendation), is increasingly likely to be recommended again by the engine, independent of the quality, value, or functionality of that product to a particular user of the engine.

This effect of conventional computer-implemented recommendation engines may be particularly undesirable to, and/or detrimental to, consumers purchasing nondurable or disposable goods intended for a personal purpose or use, such as cosmetic products, skincare products, hygiene products, food or drink products, clothing, cleaning products, and the like.

As known by many, users of conventional recommendation engines often find that recommendations provided by those engine are not suitable for them, as different users present with different medical, dietary, and/or dermatological needs, preferences, or requirements, present with different allergies to different materials or ingredients, have different preferences for the presence or absence of particular features or ingredients or additives, and so on.

BRIEF DESCRIPTION OF THE DRAWINGS

Reference will now be made to representative embodiments illustrated in the accompanying figures. It should be understood that the following descriptions are not intended to limit this disclosure to one included embodiment. To the contrary, the disclosure provided herein is intended to cover alternatives, modifications, and equivalents as may be included within the spirit and scope of the described embodiments, and as defined by the appended claims.

FIG. 6 illustrates an example recommendation matrix.

The use of the same or similar reference numerals in different figures indicates similar, related, or identical items.

Figure 1:
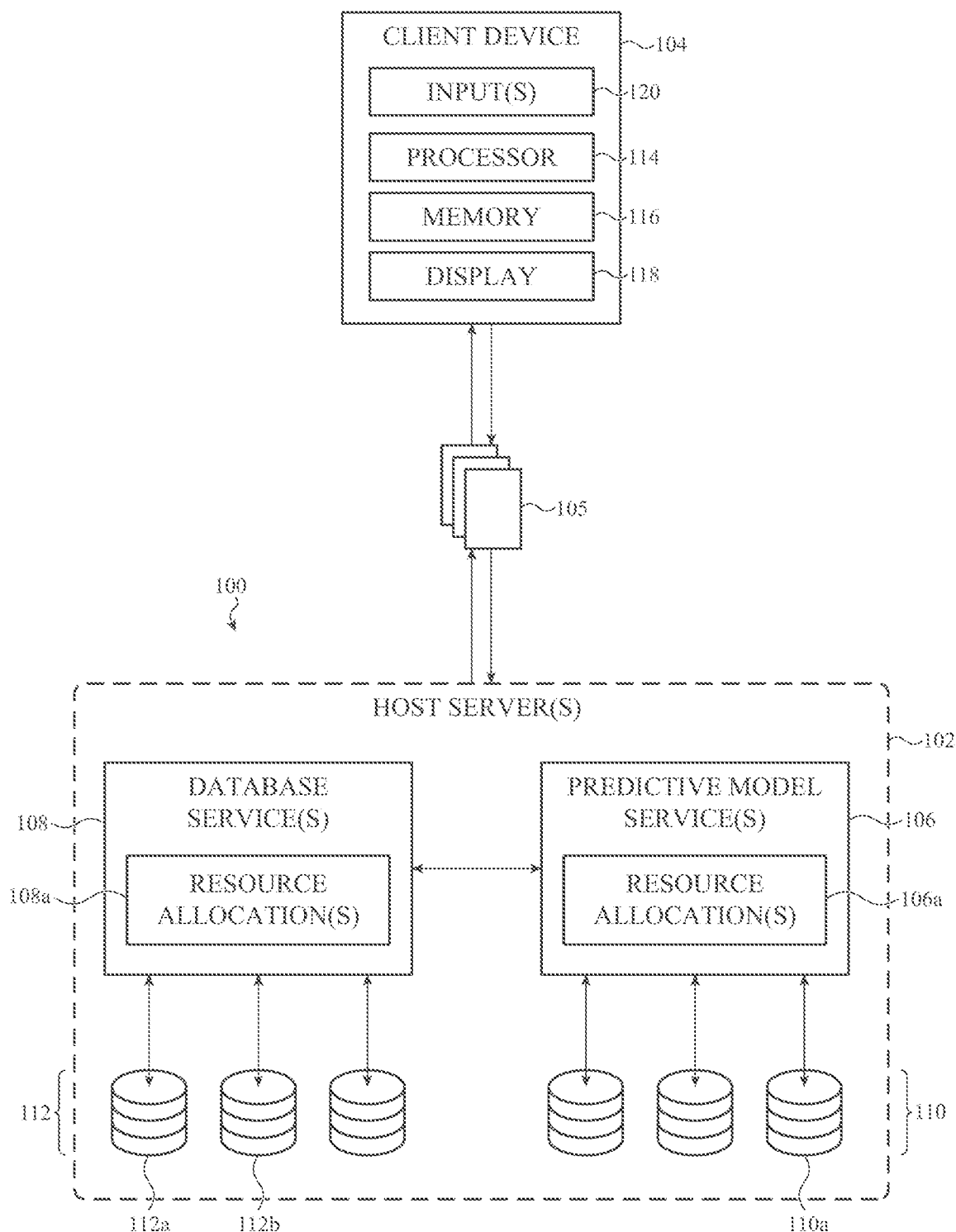
FIG. 1 is a schematic representation of a client-server architecture of a system, such as described herein.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Embodiments described herein relate to systems and methods for maintaining user privacy and/or anonymity when leveraging a user's information to generate one or more product, ingredient, and/or regimen recommendations to that user. Further embodiments described herein reference systems and methods for discovering and/or calculating correlations between very large datasets in a time, bandwidth, memory, and processor utilization efficient manner.

Generally and broadly, embodiments described herein operate by parsing customer review data of one or more products to, without limitation or express requirement: extract and/or infer demographic and environmental information from the writer of the review; generate a standardized hash (also referred to as a fingerprint, an ID, a vector, a genome, and so on) of that demographic information and environmental information such that demographically related review writers are represented by the same or a substantially similar hash (e.g., an ordered hash); extract a review sentiment and/or project that review sentiment onto a standardized graduated scale (e.g., from 0.0 to 1.0); associate the project(s) and/or regimens that are the subject of each review to a set of attributes that describe that subject (e.g., ingredients, packaging information, supply chain information, organic or animal origin information, and so on); and lastly generating a matrix data structure—referred to herein as a "recommendation matrix"—in which a first dimension is defined by a quantity of different detected demographic fingerprints among all parsed reviews, a second dimension is defined by a quantity of different detected environmental fingerprints among all parsed reviews, a third dimension is defined by a quantity of attributes describing each subject of each review.

The values of the recommendation matrix are populated with the standardized graduated scale representing review sentiment. In some embodiments, additional user-describing fingerprints can define further dimensions of the recommendation matrix. Such fingerprints can include, without limitation: location fingerprints; humidity fingerprints; temperature fingerprints; fingerprints corresponding to stress levels or ranges; fingerprints corresponding to health characteristics or parameters (e.g., overweight, underweight, hypertensive, hypotensive, and so on); medical conditions (e.g., diabetes, pregnancy status, menopause status, erectile dysfunction status, hair loss, hyperthyroid, hypothyroid, and so on); and so on.

This data architecture, which associates normalized review sentiment based on reviewer-describing information (e.g., one or more fingerprints) with product-describing information (e.g., one or more attributes, properties, ingredients, and so on), can be leveraged by other users for generating extremely user-specific recommendations. In particular, a user can provide demographic information, location information, medical information, health information, wellness information, environment information, stress information, and so on which can be used to generate a set of fingerprints, such as described above. These fingerprints can be collectively used to filter the recommendation matrix to quickly isolate the product attributes (not necessarily individual products) associated with the most-positive sentiment reviews left by reviewers who very closely match the demographic fingerprint, environmental fingerprint, medical fingerprint, health fingerprint, and so on of the user seeking the recommendation.

Once the recommendation matrix is filtered to a set of attributes associated with positive-sentiment reviews left by persons who are demographically similar, who live or occupy in similar environments, who have similar medical statuses, who have similar health statuses, who have similar body types, who have similar preferences, who currently use similar products or regimens, who have similar diets, and so on, those sets of attributes can be used to, among other things: identify a commercially available product that incorporates at least a threshold number of those identified attributes; create a custom product based on the set of attributes; create a recommendation to the user to seek out products that include some or all of the identified attributes; and so on.

In additional embodiments, the recommendation matrix can be filtered with the opposite objective; namely, the recommendation matrix can be filtered to a set of attributes associated with negative-sentiment reviews left by persons who are demographically similar, who live in similar environments, who have similar medical statuses, who have similar health statuses, who have similar body types, who have similar preferences, who currently use similar products or regimens, who have similar diets, and so on. As with the positive-sentiment example above, these sets of attributes can be used to, among other things: identify a commercially available product that incorporates at least a threshold number of those identified attributes that the user should avoid; create a recommendation to the user to seek out products that expressly do not include some or all of the identified attributes; and so on.

In additional embodiments, the recommendation matrix can be filtered with a neutral objective; namely, the recommendation matrix can be filtered to a set of attributes associated with neutral-sentiment reviews left by persons who are demographically similar, who live in similar environments, who have similar medical statuses, who have similar health statuses, who have similar body types, who have similar preferences, who currently use similar products or regimens, who have similar diets, and so on. As with the positive-sentiment example above, these sets of attributes can be used to, among other things, identify products unlikely to be either positive or negative, identify ingredients unlikely to be effective or therapeutic, and so on.

In yet further embodiments, the recommendation matrix can be additionally correlated to a diagnostic matrix that associates particular demographic fingerprints, environmental fingerprints, and so on with a likelihood of exhibiting a particular medical condition or disorder. More specifically, the diagnostic matrix can be architected in a similar manner to the recommendation matrix. In these architectures, however, in place of product/regimen attributes, diagnostic information can be used. In these examples, the diagnostic matrix can be used alongside and/or with the recommendation matrix to determine whether prescriptions should be recommended, whether a doctor's visit should be recommended, whether the user should expressly avoid or seek out particular ingredients or products, and so on.

The foregoing examples are not exhaustive; it may be appreciated that a recommendation matrix as described herein can be created, instantiated, and/or otherwise maintained in a number of suitable ways. Further, it may be appreciated that fingerprinting techniques and/or data aggregation techniques leveraged to generate a recommendation matrix can vary from embodiment to embodiment.

For example, as noted above, some embodiments can construct a recommendation matrix by receiving, as input, detailed customer review data for particular products or particular product categories. For each customer review, demographic information of the review writer is inferred as completely as possible (including, for example, age range, biological sex, and so on). Each set of demographic attributes extracted from a particular customer review is combined in a repeatable way to generate a fingerprint or hash or vector—as noted above—that collectively represents the particular collection of demographic attributes exhibited by a particular reviewer.

In other words, different reviews (on different review sites, and/or for different products) by the same reviewer should be associated with the same demographic fingerprint. Likewise, demographically similar reviewers should exhibit substantially similar or identical demographic fingerprints (i.e., in some examples a hashing function that generates a demographic fingerprint may be an ordered hashing function such that cosine distance between two demographically similar individuals is minimized and such that cosine distance—or another distance calculation—between two demographically dissimilar individuals is maximized).

In the same manner, extracted or inferred location attributes, environment attributes and so on can be likewise fingerprinted/hashed/vectorized. As such, in many examples, systems described herein can be configured to output multiple fingerprints for each processed customer review.

In addition to the fingerprint extraction/inference described above, for each customer review, sentiment information can be determined by, in some examples, semantic analysis. In other cases, a grading associated with a particular customer review can be used as a direct proxy for sentiment; a high score (e.g., 5 out of 5 stars) can be understood as a highly positive sentiment, whereas a low score can be understood as a strongly negative sentiment. In some cases, scores extracted from particular review sites and/or reviews provided by particular known reviewers may be biased upwardly or downwardly. For example, some reviewers may be overly effusive and positive; such reviews may be biased downwardly. In other examples, some reviews may be negative not because of product quality but because of a purchasing experience. In such cases, the review may be ignored and/or biased upwardly. A person of skill in the art may readily appreciate that there are many different techniques that may be used to modify graduated scale reviews left by different reviewers.

In addition to the fingerprint extraction and sentiment analysis described above, each product, service, or other thing that is the subject of each review can be captured and described as and/or associated with set of attributes describing that subject. For example, for a product containing ingredients, each individual ingredient and/or its respective proportion by volume or weight may be captured as an attribute of that product. Other product attributes can be likewise captured, such as but not limited to: product price; product size; product weight; product packaging material; product packaging material ingredients; product supply chain carbon footprint; whether the product contains organic ingredients; whether the product contains only organic ingredients; whether the product contains known allergens; what allergens are in the product; whether the product contains animal-derived ingredients; and so on. It may be appreciated that any suitable number of attributes can be used to describe a particular reviewed product.

In view of the foregoing described three datasets including one or more user-describing fingerprints (e.g., location fingerprints, demographic fingerprints, environment fingerprints), the review sentiment analysis/result, and the product attributes, a single matrix can be constructed having one dimension defined by extracted fingerprints and one dimension defined by product attributes. The values of this matrix correspond to sentiment, which may be normalized such as a float value between 0 and 1. This data structure, as described herein and as noted above, can be referred to as a recommendation matrix.

In view of the foregoing, it may be appreciated that a recommendation matrix as described herein can be leveraged to quickly and easily determine accurate and precise recommendations for a particular user looking to advance a particular personal wellness goal or looking to accommodate a particular personal preference. For example, a user may be experiencing acne and may seek out a recommendation for an acne treatment. As known to a person of skill in the art, a conventional recommendation system considers product popularity as a proxy for product efficacy, and as noted above, this is not suitable for all users or potential users of that product. In other cases, as noted above some conventional systems attempt to group similar consumers together as a collaborative filter for popular products. As with the preceding example, this technique is not suitable for all users as each user is necessarily different from others with similar spending or purchasing habits.

By contrast, embodiments described herein can leverage a recommendation matrix as described above to uncover product attributes that a particular user should seek out and/or particular product attributes that a particular user should avoid. For example, for many embodiments described herein, a user may be presented with a dynamic questionaries that elicits responses that can be used by a system as described herein to create, among other fingerprints, a demographic fingerprint for the user, an environmental fingerprint for the user, a location-based fingerprint for the user, and so on. These fingerprints can be leveraged as described above to filter the recommendation matrix and generate recommendations, both for and against particular product ingredients/attributes.

In yet other examples, user goals and/or preferences can be captured/described in a fingerprint. For example, "eliminating acne" may be a fingerprint-able data point that can be extracted from a customer review of a skincare product. In other cases, fingerprints may be more specific, such as "eliminating acne from T-Zone" may be differently fingerprinted than "eliminating acne from cheeks." Similarly, "eliminating hormonal acne" may be differently fingerprinted than "eliminating blackheads" which in turn may be differently fingerprinted than "eliminating pustules" and so on. It may be appreciated that these examples are not exhaustive.

In other cases, "reducing redness" or "decreasing dryness" may be other skincare-related fingerprint-able data points corresponding to particular user wellness goals or personal care goals. Similarly, user preferences may also be fingerprinted—preferences for or against particular color, particular fragrance, particular packaging, particular advertising copy, and so on. These examples are not exhaustive.

As noted with respect to other embodiments described herein, each of these user-specific fingerprints can be provided as input to a recommendation matrix (and/or a diagnostic matrix) such as described above which in turn can determine which attributes (e.g., ingredients, properties, and so on) of commercially-available products are likely to be most positively reviewed by the user described by those fingerprints. More specifically, a demographic fingerprint and a threshold positive sentiment score can be used to filter the recommendation matrix to a limited set of properties likely to be positively received by substantially demographically-similar users. In the same manner, a location/environment fingerprint and a threshold positive sentiment score (which may be the same or different as the demographic sentiment threshold) can be used to filter the recommendation matrix to another limited set of properties likely to be positively received by substantially environmentally-similar or location-similar users. In the same manner, a user preference and/or user goal fingerprint and a threshold positive sentiment score (which may be the same or different as other sentiment thresholds) can be used to filter the recommendation matrix to yet another limited set of properties likely to be positively received by substantially user preference and/or user goal fingerprint users.

In other cases, a matrix data structure as described herein can be filtered by a threshold negative sentiment score to identify attributes, ingredients, or other properties of a given product or service that a user having a particular demographic profile (fingerprint, hash, and so on) and/or a particular environmental profile (fingerprint, hash, and so on), and/or a particular personal care objective/goal should avoid.

In these examples, each fingerprint-filtered dataset of attributes of one or more commercially-available products can be intersected with one another to generate an extremely user-specific recommendation of product attributes. Such recommendations are based on reviews by demographically similar users, with substantially similar goals and preferences, living in similar environments, having similar diets, and so on.

Furthermore, as may be appreciated by a person of skill in the art, as a result of fingerprints described herein being ordered (in some embodiments), techniques like cosine similarity/distance can be leveraged to identify closely-related fingerprints suitable for filtering even if a particular user's fingerprints are not expressly stored or present in the recommendation matrix.

As noted above, it may be appreciated that a system as described herein can be leveraged to generate extremely user-specific recommendations. In addition, because user information is anonymized into a normalized data structure (e.g., a hash-based fingerprint), user privacy and anonymity is maintained. More specifically, even if a user's demographic fingerprint—as one example—were inadvertently disclosed, no inherent or identifying information about the user is extractable from that fingerprint, especially for embodiments in which a fingerprint is represented by a universally unique identifier or other one-way hash function. Similarly, user location information hashed into a fingerprint as described herein cannot be reversed into a location specific to any particular user.

Further still, as may be appreciated by a person of skill in the art, the described method of aggregating sets of user-describing attributes into a single fingerprint reduces the dimensional complexity of identifying correlations between user information databases and product attribute databases, such as those described herein. More simply, the hash-based indexing methods described herein dramatically increase the speed with which a computing system leveraging a recommendation matrix can obtain meaningful and user-specific recommendations therefrom. More specifically, bandwidth utilization is reduced, processor utilization is reduced, memory requirements are reduced, and requests for recommendations are serviced substantially faster than conventional database queries of multiple associated tables that require numerous computationally-expensive join/merge operations.

In view of the foregoing, more generally and broadly, embodiments described herein relate to computing systems, and methods for operating the same, configured to generate rich recommendations for users of those systems while maintaining user privacy and information security. The recommendations generated by a system as described herein can be leveraged to accommodate one or more user preferences, advance one or more express or implied user personal care goals, and/or a combination thereof.

For example, a system as described herein can be configured to provide recommendations to users for, without limitation: nutrition recommendations; vitamin/supplement recommendations; weight management recommendations; general health/well-being recommendations; hair care recommendations; hair product recommendations; hair color recommendations; fragrance and parfum recommendations; bath and body care recommendations; family/dependent care recommendations including child health, child wellness, child supplementation recommendations, infant and/or toddler nutrition, infant and/or toddler skincare or skincare; sexual wellness recommendations; birth control recommendations; beauty procedure recommendations; beauty/aesthetic procedure recommendations; plastic and cosmetic surgery recommendations; color cosmetic recommendations; makeup recommendations; pet healthcare recommendations; pet supplementation and nutrition recommendations; pet selection recommendations; entertainment recommendations (including child toys and pet toys); food and drink recommendations; oral care recommendations; exercise recommendations; holistic life/wellness improvement recommendations; mental health recommendations; addiction care recommendations; fabric care; laundry products; detergents; and so on.

More broadly, embodiments described herein may be understood to be applicable to provide recommendations through a wide spectrum of product, service, regimen, and/or lifestyle areas.

In many cases, a system as described herein may be configured to provide multiple cross-category recommendations that cooperate in one manner or another to improve one or more aspects of a user's health, wellness, and/or to accommodate one or more user preferences. For example, two users with identical demographic fingerprints may have different preferences for fragrance. In this example, a preference fingerprint for these users will be different and thus despite identical demographic fingerprints, these two users may be presented with different recommendations.

Similarly, two users with identical demographic fingerprints, and identical personal care goal fingerprints, may live in different environments and thus may be associated with different environmental fingerprints. In this example, product recommendations may differ by environment (e.g., a first environment may have a higher UV index, a second environment may have a much higher average pollution or humidity, and so on).

Further to the previously described examples, many embodiments described herein are configured to collect and aggregate attributes of, and/or describing, one or more personal care goals, one or more personal preferences, and demographic information (e.g., user information, user location/environmental information, current products and/or ingredients used, and so on) of a particular user and to correlate co-occurrences of two or more of those attributes against a dataset or database of product attributes (e.g., active and inactive ingredients, sources, supply chain participants, purchase availability, packaging materials, ingredient proportions and volume) and product use/regimen attributes (e.g., use frequency, manner of use, and so on) to generate a listing of product attributes most correlated to, and/or most likely to elicit a positive review from, the user. Thereafter, this listing of product attributes can be used to, in some examples, identify a commercially-available product to recommend to the user (e.g., a product containing at least a threshold number or percentage of the identified product attributes), create and recommend a custom-blended product for the user, create and/or recommend a change in regimen and/or a substitution of a current product for another or a currently-used ingredient for another, and so on.

In this manner, and as a result of the embodiments described herein, a user can be provided with product and/or ingredient and/or regimen recommendations that accommodate both user preferences and needs, while expressly avoiding any negative effects that may result from that same user feeling uncomfortable sharing personal preference/goal information with advertisers or real human persons.

Further, as correlations between user-side aggregated attributes and product-side aggregated attributes may change over time, recommendations provided by a system as described herein can be leveraged on a continuing basis to provide up-to-date recommendations to a user to both accommodate changes to express or implied preferences and/or to advance changing or adapting express or implied personal care goals.

For example, in some embodiments, a user may leverage a system as described herein to advance a personal care goal related to a skin condition. The user may express a concern related to skin dryness. In this example, a system described herein may be configured—as described in detail below—to obtain and/or collect demographic information from the user, to obtain and/or collect environmental information from the user (e.g., residence address, work address, commute type, and so on), and may collect and/or otherwise obtain information concerning the user's skin concern.

In this example, the system as described herein may be configured to correlate attributes of the user's skin, environment, and demographic history to a database of ingredients used in skincare products, each ingredient being associated with a sentiment score (e.g., positive sentiment, negative sentiment, neutral sentiment) based at least in part on aggregated reviews associated to products containing those ingredients, such as described above. Based on this correlation, a system as described herein can identify a set of ingredients associated with positive sentiment that correlate to the user's particular demographics, environment, and skin concern. Thereafter, a custom-formulated skincare product can be formed based on the list of ingredients (and/or proportions thereof) and the user can be provided with that product.

In further examples, the system can be configured to proactively update the correlation(s) that informed the custom-formulated product (e.g., on a schedule, at a particular interval, and so on). For example, review sentiment associated with a particular product or ingredient may shift over time which in turn may cause a system as described herein to automatically adjust ingredient proportions and/or mixtures. In other cases, the user's environment may change (e.g., seasonally, as a result of a move, and so on) and the change may cause a system as described herein to automatically adjust ingredient proportions and/or mixtures. In a more simple phrasing, as a result of the correlation operations described herein across multiple attributes, a system as described herein can be leveraged to automatically update user-specific recommendations, whether those recommendations are directly or indirectly related to a particular personal care goal or personal preference of the user.

In further embodiments of the foregoing example, a system as described herein may be further configured to provide additional recommendations, not directly related to a stated user goal or preference. For example, if a user expresses a skin concern related to dryness, the system may operate as described above to identify ingredients that may be therapeutic to the user's concern. The system may likewise identify ingredients that may exacerbate the user's skin concern as ingredients the user should avoid. Likewise, the system may identify ingredients that, if used separately, may be therapeutic to the user's skin concern, but if used together may interfere with one another. In addition, the system may be configured to recommend the user use a humidifier, reduce shower temperature, increase water consumption, supplement with a particular nutrient, and so on.

For simplicity of description, many embodiments that follow reference an implementation in which a recommendation matrix as described herein is leveraged to provide skincare product recommendations. However, it may be appreciated that this is merely one example implementation and that in many embodiments, other recommendations (unrelated to, or only indirectly related to, skincare) may be generated by a system as described herein.

For example more generally, as noted above, systems described herein leverage a matrix data structure to facilitate computationally efficient and fast comparisons between large attribute datasets. In particular, as noted above, a first dataset may include user-specific attributes and data points. As a simple, non-limiting example, a first database including user information can include one or more associated tables, each configured to store attributes related to a particular user.

For example, a first table may be configured to store environmental attributes such as pollution index (including light pollution), seasonal temperature averages, seasonal humidity averages, UV index, zip code, postal codes, and so on. Tables associated to this table may include attributes such as UV index by month of year, pollution by month of year, pollen count by month of year, and so on. A second table may store information related to the user, such as demographic information including age, biological sex, height, weight, ethnicity, and/or medical information such as Boolean values noting particular health conditions, allergies, and so on.

Yet other tables can be configured to store information related to user preferences such as preferences for or against: particular ingredients; particular supply chains (e.g., countries of origin, carbon footprint of supply chain); particular colors; particular fragrances/aromas; particular packaging materials; and so on.

Other sets of tables can include information related to particular commercially-available products, ingredients therein, and/or reviews describing personal experiences with those products. More particularly, reviews can be scraped from one or more review sources (e.g., online retailers of such products) and analyzed to determine attributes thereof. For example, a review text can be reviewed to infer demographic information of the review writer, geographic information of the review writer, sentiment of the review writer, regimen information of the review writer, and so on.

In many embodiments, such as described herein, the demographic information inferred from a particular review can be collapsed into a single identifier, fingerprint, genome, or hash that corresponds to a particular collection of demographic, environmental, or other variables. For example, a demographic fingerprint might include information such as biological sex, age range, hair color, current products/ingredients used, current supplements/medications used (and dosages), activity level, digital device usages, and ethnicity. In this example, a code such as "F2530RC" may be used to represent a demographic group of female persons, aged 25-30 with red hair who are Caucasian. In some examples, although not required, this code may be provided as input to a one-way hash function so as to increase information security and user information privacy.

Another code may be "F3040BrA" which may be used to represent a demographic group of female persons, aged 30-40, having brown hair, and being of Asian descent. Yet another code may be "NB3040BrC" which may be used to represent a demographic group of nonbinary persons, aged 30-40, having brown hair, and being of Caucasian descent. Yet another code may be "M2030BA" which may be used to represent a demographic group of male persons, aged 20-30, having black hair, and being of sub-Saharan African descent. As with previously examples, although not required, these codes may be provided as input to a one-way hash function so as to increase information security and user information privacy.

In many embodiments, such codes or fingerprints representing particular demographic groupings can be hashed so as to generate universally unique identifiers that correspond to a particular collection of demographic attributes. These hashes can dramatically increase the efficiency and speed with which matrix operations, as described below, are calculable. More specifically, as may be appreciated by a person of skill in the art, by collapsing groupings of co-occurring attributes together into a single value, dimensional complexity of a matrix operation is reduced.

In a similar manner, an environmental fingerprint might include information such as seasonal temperature average ranges, seasonal humidity average ranges, seasonal UV index averages ranges, and so on. For example, an environmental fingerprint might be represented as a structured object such as (formatted in this examples as a JSON object):

```
{
  "Q1": {
    "temp" : [70, 80],
    "hum" : [30, 50],
    "UV" : [3,7]
  },
  "Q2": {
    "temp" : [50, 70],
    "hum" : [10, 30],
    "UV" : [0,2]
  },
  "Q3": {
    "temp" : [40, 50],
    "hum" : [0, 40],
    "UV" : [4,7]
  },
  "Q4": {
    "temp" : [50, 70],
    "hum" : [10, 30],
    "UV" : [0,2]
  },
}
```

This foregoing data structure can represent an environment in which calendar quarter 1 typically has a temperature average ranging from 70-80 degrees, a humidity average ranging from 30-50%, a UV index ranging from 3 to 7, and so on. As with preceding examples, in many embodiments, such codes or fingerprints representing particular environmental groupings can be hashed so as to generate universally unique identifiers that correspond to a particular collection of environmental attributes.

In yet other examples, other data can be hashed into an environmental fingerprint including, but not limited to: pollen count; pollution; blue light exposure (e.g., computer time); population density; community spread of communicable disease; toxic chemical exposure risk; wildfire exposure risk; windspeed averages (e.g., windchill averages); volatile organic compound counts/ranges; carbon dioxide counts/ranges; and so on. These are not exhaustive.

Still other attribute groupings can be grouped together to form discrete fingerprints/genomes as described above. Examples include, pollution fingerprinting, weather fingerprinting, diet fingerprinting, holistic health fingerprinting, cardiovascular health fingerprinting, pulmonary health fingerprinting, addition status fingerprinting (e.g., opiate addition status, alcohol use status, tobacco use status, marijuana use status, and so on), prescription medication status fingerprinting, vaccination status fingerprinting, and so on.

Further it may be appreciated that these foregoing examples are not exhaustive; any suitable collection of attributes of a person, personal preferences, lifestyle, health, fitness, wellness, mental wellbeing (resulting from testing, professional opinion, or the like), and so on can be fingerprinted in the manner(s) described herein. In other cases, genetic or hereditary factors, personal goals or objectives, lifestyle attributes (e.g., sedentary vs. active, diabetic status, genetic history, and so on), gut or skin or dental microbiome factors, environmental factors (e.g., weather, seasonal shifts, and so on), results of one or more lab-conducted or in-home conducted tests (e.g., microbiome tests, genetic tests, urine tests, blood tests, saliva tests, and so on), and so on.

In yet other examples, machine learning and/or computer vision can be leveraged to inform one or more attributes describing a person based on a photo or video (in any suitable spectrum, including ultraviolet, color, infrared, and so on). For example, computer vision may be leveraged to infer a person's ethic background, skin quality, color, or type, gender, and so on. In other cases, computer vision may be leveraged to identify acne, dry skin, oily skin, freckle/mole density, rosacea, and so on. Each of these examples can be used to inform one or more attributes describing a person as described herein.

Further, the concept of fingerprinting as described above can likewise be applied to attributes of individual products. For example, common groupings of ingredients can be used to define a fingerprint as described above, which in turn can be collectively represented as a single attributed in a recommendation matrix as described herein. In another example, attributes of packaging, supply chain, animal origin, non-GMO origin, and so on, can be used to generate a number of individual fingerprints that describe a particular product and can be incorporated into a recommendation matrix as described above.

In view of the foregoing description, it may be appreciated that a system as described herein can be operated to associate particular fingerprints/genomes with positive and/or negative sentiment product reviews, which in turn can be used to isolate particular ingredients (or, more generally, particular attributes) of particular previously-reviewed products (having one or more product attribute fingerprints) that are positively reviewed by certain "fingerprinted" reviewers and particular ingredients/attributes that are negatively reviewed by certain "fingerprinted" reviewed. More generally, a system as described herein can be configured to determine associations between particular fingerprints and particular attributes of individual reviewed products.

In addition, as noted above, a review grading can be recorded and, in some cases, normalized to a consistent scale. For example, one review site may permit reviewers to rank an experience from 1-5 stars, whereas another website may be configured to permit reviewers to rank an experience with a particular product from 1-10 stars, whereas another website may be configured to permit reviewers to rank an experience with a particular product with an A to F grade, whereas another website may be configured to permit reviewers to rank an experience with a product in another manner. Each of these may be normalized to a standard scale, such as a scale of 1 to 5 or on a scale from 0 to 1 or on a scale of −100 to 100. Any suitable normalized graduated scale is possible.

In this manner, a system as described herein scraping product reviews can be configured to receive a review text as input, and can be configured to provide as output a table or table row that includes inferred demographic information of the reviewer, inferred environmental information of the reviewer, and (at least) an identification of the product(s) that is the subject of the review. This dataset can thereafter be associated to one or more additional tables that each store one or more attributes of the product that was the subject of the review. For example, a first table may store ingredient information about consumable products that may be reviewed by a reviewer. Another table can store one or more packaging attributes (e.g., product size, container shape, container volume, price, geographic availability, country of origin, carbon footprint, and so on) of the product that is the subject of a review.

This collection of aggregated information can be joined together in order to form a recommendation matrix, as described herein. This recommendation matrix can be leveraged as described herein to, in one example, generate user-specific custom skincare recommendations.

For example, as known to a person of skill in the art, users of skincare products may have widely varying knowledge bases regarding the types of skincare products that may be appropriate for the skin of the particular user. For example, the skin of a 15 year-old female user may be significantly different than the skin of a 36 year-old male. The two skin types may vary in a number of ways, including the oil production by the skin and other factors such as sun exposure, yet these two users may select the same skincare product off the shelf of a department store based on marketing materials, sales associate recommendations or placement within the store.

Further, even though the 36 year-old male may be more aware of his skincare needs than the 15 year-old female, and even though they may base their skincare product selections on completely different criteria, both still may end up selecting the same skincare product due to the limited nature of currently available skincare products available for purchase. Although the same skincare product may be effective for the 15 year-old female and the 36 year-old male, in many cases the product may be more effective for one person than the other and/or may exacerbate different issues for each person.

Further still, the sellers of the skincare products or other self-identified experts may have a varying knowledge base of the different product lines, what the different products are typically used for and may have little knowledge regarding the intricacies of a particular user's skincare needs, history, allergies, reaction history, and so on. Similarly, dermatologists and other professionals may be highly influenced by pharmaceutical sales representatives and may not fully understand the set of ingredients in a particular product that is advertised with only a few active ingredients emphasized.

As a result, many skincare experts—regardless whether those experts are sales persons, self-appointed experts, or degree-baring experts—may recommend a product that can be detrimental for a user due to a general lack of specific knowledge of the product and/or the user, and/or the potential for the product to interfere with or interact with other products the user applies or consumes. Such recommendations may present drawbacks to the user such as paying for a product with no visible results, worsening skin conditions, and undesired skin reactions, among others.

The following disclosure generally relates to systems, process flows, and methods for recommending and providing a personalized skincare product or product line to a user, where the personalized skincare product line is specifically formulated for the user based on user information, environmental information, location information, user preference information, user goal information and the like.

User information may include skin related factors and non-skin related factors. The skin related factors may include information regarding oil production of the user's skin, allergies to ingredients, specific skin issues such as rosacea, acne, eczema, hyperpigmentation, fine lines, dark circles under the eyes, premature wrinkles, puffy eyes, crepey skin, or any combination thereof, and so forth. Non-skin related factors may include information regarding the geographic region in which the user resides, water intake, activity level, sun exposure, pollution levels, water hardness, or any combination thereof, and so forth. Skin related factors and non-skin related factors will be discussed in further detail herein.

This disclosure relates to systems, process flows, and methods for providing a curated skincare regimen recommendation for a user, based at least partially on a one or more fingerprints related to the user defined by at least one fingerprint, such as described above (e.g., demographic fingerprint, skin-type fingerprint, environmental fingerprint, and so on).

More specifically, the disclosure relates to employing a user profile matrix and a corresponding user's associated fingerprint(s) to identify particular ingredients that can be incorporated into (and/or should not be incorporated into) a set of curated products for a user.

The user profile matrix may be one way of documenting a user's associated fingerprint(s). The user profile matrix may be a multidimensional matrix, in that different data points of the user's associated fingerprint(s) may indicate an intersection or correlation of two, three, or more skincare factors.

For example, a user's associated fingerprint(s) may include the correlated or intersecting skincare factors of being 19 years old, having oily skin, and living in a high humidity climate. Although each of these factors may be accounted for individually in multiple skincare products, when the intersecting skincare factors are simultaneously accounted for, a more effective skincare recommendation and product or product line may be provided to the user.

Further, the user profile matrix and correspondingly, the user's associated fingerprint(s) may be used to identify which ingredients which may best address the intersecting skincare factors of the user. In some examples, the ingredients may be categorized into base ingredients and additive ingredients. The base ingredients may be referred to herein as foundation ingredients and the additive ingredients may be referred to herein as additives or "boosters".

As one non-limiting example, individual user data may be received and a one or more fingerprints related to the user may be generated from this user data. The individual user data may include information received from the user, who may be responding to a dynamic survey or questionnaire. In some examples, the dynamic questionnaire may ask questions in an order and with content specific to the user answering those questions.

The dynamic questionnaire may be configured to present follow-up questions, to omit irrelevant questions (as determined by user input, user demographics, and/or answers to previously-presented questions), to ask supplemental questions, and so on. In some examples, the questions may be directed to skin conditions such as rosacea or eczema, skin issues such as dark spots or wrinkles, skin concerns such as aspects of their skin with which the user may be concerned, skin type such as oily, dry, combination, and so forth. Even though an aspect of the user's skin such as dark spots may be categorized as a skin issue, it may also fall into other categories such as a skin condition and a skin concern.

The one or more fingerprints related to the user may be an entry in a client or customer database, which may be stored on, for example, a host server (more generally, a "computing system"). The one or more fingerprints related to the user may be further documented in a user profile matrix which may include a set of user-specific attributes. The user-specific attributes may include skin related factors and non-skin related factors which may affect the skin of an individual. The one or more fingerprints related to the user may be mapped to the relevant user-specific attributes to produce the user profile matrix.

A user's associated fingerprint(s) may then be derived from the user profile matrix. The user's associated fingerprint(s) may be a string of characters which may be representative of skin issues, conditions, and concerns of the user, along with any other relevant data such as seasonal changes, altitude, water alkalinity which may affect the user's skin.

Using this user's associated fingerprint(s), an individualized curated skincare product ingredient set and/or product line may be created and/or selected for the user from a set of base ingredients and a set of additives custom-selected for the user. The curated skincare product line may be recommended to the user and provided to the user for purchase. In some examples, the skincare product line may include one or more of a facial cleanser; a topical sunscreen; a topical serum; an exfoliator; a moisturizer; a chemical peel; a toner; an eye cream; a night cream; or any combination thereof, and so forth, each of which may have different ingredients, ingredient proportions, and/or may be configured to cooperate to advance one or more skin goals or preferences expressed by the user.

Selecting a curated skincare ingredient set that informs customization of a curated product line according to the specific needs and issues of a user provides beneficial advantages to the user. For example, the curated skincare product line may be adaptable according to the one or more fingerprints related to the user. In some examples, the one or more fingerprints related to the user may include information regarding seasonal changes which correspond to where the user resides.

The curated skincare product line may include different ingredients and may be adapted to the specific weather conditions of the user's geographic region. Some users may live in the southern part of the United States by the coast with high humidity and warm weather and other users may live in a landlocked state with very low humidity and a wide range of weather from below freezing to high altitude sun exposure. The ingredients of the curated skincare product line may change or be updated according to the temperature variations (e.g., seasonally), the humidity variations, and the general sun exposure experienced by the user over the course of a year. By changing the ingredients and/or combinations or proportions thereof of one or more products of the curated skincare product line, the products may address, mitigate and/or prevent specific issues that a user may experience.

These and other embodiments are discussed below with reference to FIGS. 1-9. However, those skilled in the art will readily appreciate that the detailed description given herein with respect to these figures is for explanatory purposes only and should not be construed as limiting.

FIG. 1 is an example recommendation engine that can instantiate a recommendation matrix, such as described herein. In the illustrated embodiment, the recommendation engine 100 is implemented with a client-server architecture including a host server 102 (more generally, a "computing system") that communicably couples (e.g., via one or more networking or wired or wireless communication protocols) to one or more client devices, one of which is shown as the client device 104. The client device 104 and the host server 102 of the recommendation engine 100 can be configured to transaction information, identified as the data items 105, such as, but not limited to: user demographic data; user geographic data; user location data; user environmental data; user preference data; user goal data; and so on. More particularly, the client device 104 can be configured to transmit to the host server 102 a fingerprint calculated/determined by the client device 104. In other cases, the client device 104 can be configured to transmit one or more sets of attributes such as demographic attributes, environmental attributes, preference attributes, goal attributes, and so on.

It may be appreciated that other client devices may be configured in a substantially similar manner as the client device 104, although this may not be required of all embodiments and different client devices can be configured differently and/or may transact data or information with, and/or provide input(s) to, the host server 102 in a unique or device-specific manner.

More specifically, the host server 102 can be configured to leverage one or more processor allocations or processing resources to load from a non-transitory memory allocation or resource at least one executable asset, such as a binary file, source code, and the like. The processor allocation can cooperate with the memory allocation to instantiate an instance of backend software configured to provide an interface with which corresponding frontend instance of software can communicate.

The client device 104 can be any suitable personal or commercial electronic device and may include, without limitation or express requirement, a processor, volatile or non-volatile memory, and a display. Example electronic devices include, but are not limited to: laptop computers; desktop computers; wearable devices; cellular phones; tablet computing devices; and so on. It may be appreciated that a client device 104, such as described herein, can be implemented in any suitable manner.

In many embodiments, the processor of the client device 104 can be configured to execute and/or instantiate an instance of an application (herein referred to as a "client application") stored, at least in part, in memory. In particular the client device 104 can be configured to leverage a processor thereof to access a memory thereof to retrieve from the memory at least one executable asset (e.g., source code, binary files, and so on) and by interoperation with the memory instantiate an instance of the client application. The client application can be a browser application, a native application, or a combination thereof. The client application can be configured to provide frontend functionality for a recommendation engine as described herein. More specifically, the frontend application can be configured to communicably intercouple to a backend instance of software hosted by the host server 102.

More generally, the client application can be configured to access and communicate with the host server 102 and to securely transact information or data with, and provide input(s) to, the host server 102. As noted above, in some embodiments, the client application may be a browser application configured to access a web page or service hosted by the host server 102 that is accessible to the client device 104 over a private or public network that may, in some embodiments, include the open internet.

In many embodiments, the host server 102 is configured to operate within or as a virtual computing environment that is supported by one or more physical servers including one or more hardware resources such as, but not limited to (or requiring) one or more of: a processor; a memory; non-volatile storage; networking connections; and the like. For simplicity of description and illustration, these example hardware resources are not shown in FIG. 1.

In many embodiments, the host server 102 can include a number of discrete subservices or purpose-configured containers or virtual machines each configured to perform, coordinate, serve, or otherwise provide one or more services, functions, or operations of the host server 102, such as (1) serving a questionnaire to a user/user operating the client device 104, (2) receiving a response from the client device 104 containing user data (e.g., geographic data, questionnaire responses, demographic data, preference data and so on), (3) determining a diagnosis of one or more skin concerns presented by the user by leveraging a predictive model trained by information obtained from at least customer review data scraped from a public resource, (4) determining a user-specific ingredient list by leveraging a predictive model 106 trained by information obtained from at least customer review data scraped from a public resource, and (5) determining or selecting a skincare product base and one or more skincare product additives that can be mixed together to create a user-specific skincare product. In addition, the host server 102 can be configured to generate training data and to train the one or more predictive models.

To perform these and other operations, the host server 102 of the recommendation engine 100 can functionally subdivided into one or more purpose-configured modules or services. For example, in many embodiments, the host server 102 includes a predictive model service 106 and a database service 108, which may be communicably coupled to each other and/or to one or more other services or functional elements of the host server 102 (not shown).

The predictive model service 106 of the host server 102 can be configured to host and/or otherwise service requests to access one or more predictive models that may be trained in a particular manner and/or may serve a particular function. In other cases, the predictive model service 106 may also be configured to provide access to a consumer review predictive model configured to ingest a diagnostic matrix, a user dataset and/or other information, and to output a customer review prediction matrix, entries of which correspond to probabilistic assessments of likelihood that a particular ingredient, if used by the user in a recommended manner, would elicit a positive product review from that user.

In still further embodiments, the predictive model service 106 can be configured to provide access to other predictive models, trained in any suitable manner. In many cases, a predictive model served by the predictive model service 106 of the host server 102 can be stored in any suitable form or format in a database accessible to the predictive model service 102, such as the databases 110, one of which is identified as the model database 110a. The predictive model service 106 and the various functions and operations thereof are described in greater detail with reference to embodiments that follow.

The database service 108 of the host server 102 can be configured to host and/or otherwise service requests to access to one or more databases or data sources, internal or external to the host server 102. Example databases, access to which is facilitated and/or controlled by the database server 108 are illustrated as the databases 112 and can include, without limitation: an ingredient interaction database 112a; a drug interaction database 112b; an ingredient database; a product database; a customer review database; a scientific journal or study information database; and so on. In many cases, the database service 108 of the host server 102 can be configured to access one or more remote or third party databases to obtain information.

Examples of a third party database that may be accessed by a database service, such as described herein, includes: a water hardness database; a weather prediction database; a customer database; a customer review database; a scientific journal or study database; and the like. The database service 108 and the various functions and operations thereof are described in greater detail with reference to embodiments that follow.

Each of the predictive model service 106 and the database service 108 are associated with allocations of physical or virtual resources (identified in the figure as the resource allocations 106a and 108a respectively), such as one or more processors, memory, and/or communication modules (e.g., network connections and the like), that such an implementation is not required. More generally, it may be appreciated that the various functions described herein of a host server 102 can be performed by any suitable physical hardware, virtual machine, containerized machine, or any combination thereof.

Similarly, it may be appreciated that the client device 104 can be implemented in a number of suitable ways. In one embodiment, the client device 104 includes a processor 114, a memory 116, a display 118, and an input sensor or input device 120. These components can cooperate to perform or coordinate one or more operations of the client device 104 as it communicates with and transacts information with the host server 102.

The foregoing embodiment depicted in FIG. 1 and the various alternatives thereof and variations thereto are presented, generally, for purposes of explanation, and to facilitate an understanding of various configurations and constructions of a system, such as described herein. However, it will be apparent to one skilled in the art that some of the specific details presented herein may not be required in order to practice a particular described embodiment, or an equivalent thereof.

Figure 2A:
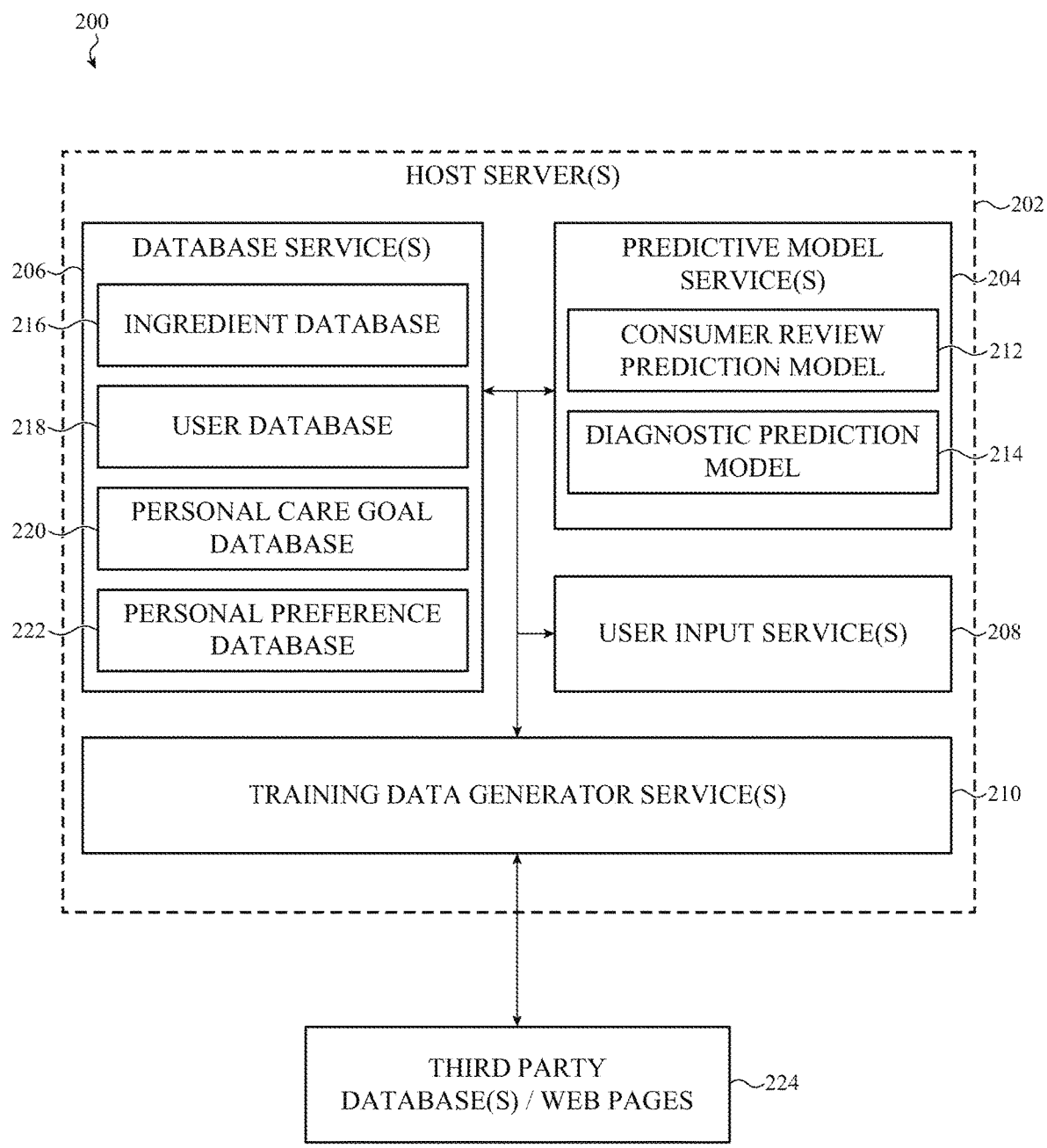
FIG. 2A is a schematic representation of a host server of the client-server architecture of the system of FIG. 1.

FIG. 2A is a schematic representation of a host server of the client-server architecture of the system of FIG. 1. In this embodiment, the recommendation engine 200 includes a host server 202 which, in turn, is defined by a number of discrete and purpose-configured components. In particular, the host server 202 can include a predictive model service 204, a database service 206, a user input service 208, and a training data generator service 210.

As noted with respect to other embodiments described herein, the predictive model service 204 of the host server 202 can facilitate access to and data transactions with one or more predictive models, such as a consumer review prediction model 212 and a diagnostic prediction model 214.

As noted with respect to other embodiments described herein, the consumer review prediction model 212 can be configured, in some embodiments, to perform an operation to assess a statistical likelihood that a particular ingredient, if used by a particular user, is likely to elicit a positive review from that user with respect to a skin concern of that user.

As noted above, the consumer review prediction model 212 can be trained with data extracted from one or more public and/or private databases comprising consumer reviews of skincare products. In particular, the consumer review prediction model 212 can be trained to determine correlations between demographic and geographic data associated with an author of a review, the ingredient set of a product that is the subject of that review, and one or more skin concerns or conditions mentioned in that review.

Once trained on a sufficiently large dataset (which may vary from embodiment to embodiment), the consumer review prediction model 212 can predict whether a given user exhibiting a skin concern is likely to successfully treat the condition associated with a specific ingredient. The various functions and operations of a consumer review prediction model—which itself may leverage a recommendation matrix such as described herein—, such as the consumer review prediction model 212 depicted in FIG. 2 are described in greater detail below.

Similarly, the diagnostic prediction model 214 can be configured, in some embodiments, to perform an operation to assess a statistical likelihood that a particular user dataset consumed by the model corresponds to a user that presents with a specific given skin concern. More generally, the diagnostic prediction model 214 can be configured to output a diagnostic matrix, each entry of which corresponds to a statistical assessment or prediction of a likelihood that a skin concern associated with that particular entry is presented by a given user. As noted above, the diagnostic prediction model 214 can also be trained with data extracted from one or more public and/or private databases comprising consumer reviews of skincare products (and/or scientific journal or study data).

In particular, the diagnostic prediction model 214 can be trained to determine correlations between demographic and geographic data associated with an author of a review and one or more skin concerns or conditions mentioned in that review. Similar to the consumer review prediction model 212, once trained on a sufficiently large dataset, the diagnostic prediction model 214 can predict whether a given user exhibits or is likely to present with one or more skin concerns. The various functions and operations of a consumer review prediction model, such as the diagnostic prediction model 214 depicted in FIG. 2, are described in greater detail below.

As noted with respect to other embodiments described herein, the database service 206 of the host server 202 can facilitate access to, and data transactions with, one or more databases such as, but not limited to: an active and/or inactive ingredient database 216; a customer database 218; a personal care goal database 220; and/or a personal preference database 222.

In one embodiment, the active and/or inactive ingredient database 216 is configured to store information related to ingredients that may be used in one or more skincare products, whether customized or otherwise. Information contained in the active and/or inactive ingredient database 216 can include, but may not be limited to: an ingredient name; an ingredient identifier; an ingredient status identifier (e.g., active or inactive); an ingredient source; an environmental impact metric of an ingredient; a price per unit of the ingredient; allergy information associated with the ingredient; interaction information associated with the ingredient; an ingredient description; a list or identifier of a skin concern for which the ingredient is therapeutic or otherwise beneficial; and so on and the like.

The customer database 218 can be configured in any suitable manner to store user data and/or demographic data or environmental/location/geographic data. Examples include, but are not limited to: a user name; a user age; a self-reported user skin type; a user skin concern (or set of skin concerns or unique identifier corresponding to a set of skin concerns); an ethnicity or set of ethnicities; a geographic location of the user; and so on. In many cases, the customer database 218 can store historical information as well, noting and recording changes in a user's skincare recommendations and/or changes in demographic or geographic data over time.

The personal care goal database 220 can be configured in any suitable manner to store information related to not necessarily medical skin concerns identified by a user (e.g., redness, dryness, texturing, crepeyness, and so on) and/or medical conditions that can be diagnosed by the recommendation engine 200 or, more particularly, diagnosed and/or otherwise recognized by the diagnostic prediction model 214 of the predictive model service 204 of the host service 202. In many embodiments, the personal care goal database 220 is configured to store, without limitation: a skin concern identifier; a skin concern sign list; a skin concern symptom list; a set of one or more diagnostics that, if exhibited by a user, increase a statistical likelihood that the user exhibits the skin concern; and so on.

The personal preference database 222 can be configured in any suitable manner to store information related to personal preferences that may be unrelated to a particular skin condition or concern. For example, some users may have preferences for or against (without limitation): products with organic ingredients only; products preferring organic ingredients; products with non-GMO ingredients only; products in which GMO ingredients are acceptable; products marketed in a particular manner; products from a particular country of origin; ingredients of a particular origin; packaging materials that are recyclable; products manufactured and/or shipped with particular carbon footprints and/or via particular channels; products manufactured with particular labor standards; products of particular size; products with particular shelf life; products within particular price brackets; products endorsed or not endorsed by particular persons or organizations; products manufactured with particular materials (e.g., BPA, plastics, and so on); and the like. In some cases the personal preference database 222 may also store information related to non-medical look and feel of a particular product, such as (but no limited to): a preference for or against colorants; a preference for or against abrasives; preferences for or against particular textures (e.g., oily, abrasive, smooth, matte, dry, alcohol-based, and powdery, and so on); preference for or against particular skin-feel, application method, or post-application appearance (e.g., matte, powdery, smooth, translucency, opalescence, white caste, serum-like, creaminess, liquid-based, stick-based foundation, propensity for drying, propensity for moisturizing, propensity for pilling, tint colorfastness, propensity to cause glass skin appearance, radiance, and so on); preference for or against particular coverage (e.g., high, medium, low); preference for or against particular longevity; need to reapply; meltiness; waterproofing, water-fastness; water-based; oil-based; powder-based; serum-based; and so on.

In further embodiments, the database services 206 can include other databases, such as databases that can be configured in any suitable manner to store information related to statistical likelihoods of a particular skin concern occurring with another skin concern based on population data and/or demographic data of users exhibiting said conditions. In this configuration, the personal preference database 222 can be leveraged by the host service 202 to determine which diagnosis among a set of diagnoses output by the diagnostic prediction model 214 via a diagnostic matrix are more likely to be correct diagnoses than others.

The training data generator service 210 of the host server 202 can be configured to iteratively or otherwise obtain training data to update training of one or more of the models of the predictive model service 204. In particular, in many embodiments, the training data generator service 210 is configured to scrape information from publicly-accessible consumer review and/or scientific dermatological study/survey databases (collectively identified as the third party databases 224) and to extract data from those databases to generate training data that correlates particular demographic characteristics (of the authors of customer reviews and/or of the subject(s) of scientific studies) and one or more therapeutic or otherwise beneficial active or inactive ingredients of the product(s) that are the subject of those reviews/studies. The various functions and operations of a training data generator service, such as the training data generator service 210 depicted in FIG. 2 are described in greater detail below.

It may be appreciated that the foregoing description of FIG. 2, and the various alternatives thereof and variations thereto, are presented, generally, for purposes of explanation, and to facilitate a thorough understanding of various possible configurations of a recommendation engine, such as described herein.

However, it will be apparent to one skilled in the art that some of the specific details presented herein may not be required in order to practice a particular described embodiment, or an equivalent thereof. For example, it may be appreciated that the host service 202 depicted in FIG. 2 can be configured to transact information with the client device 104 to provide recommendations to a user operating the client device 104 in a number of suitable ways.

For example, although many embodiments described above reference skincare, this is merely one example. In other cases, a system as described herein can be configured to leverage a recommendation matrix and/or an architecture as described above to generate other attribute-based recommendations that are specifically tailored to a particular user.

For example, in some embodiments, the recommendation engine 200 can be configured to provide user-specific recommendation related to nutrition and/or supplementation. The system can be configured to receive demographic and/or location information from a user to generate a listing of user-describing fingerprints/attributes such as described above, some of which may relate to a user's preference for or against particular methods of receiving nutritional supplements. For example, some users may have a preference for capsules, whereas others may have a preference for powders. Others still may have a preference for diet-shifting recommendations. In these examples, the recommendation engine 200 can be configured to instantiate a recommendation matrix correlating product reviews and/or including particular nutrients with user-describing fingerprints, such as described above. In this manner, the recommendation matrix can be leveraged to recommend to a user (or recommendations against) one or more ingredients, one or more user-custom products (or collections of products), and/or one or more consumer products (or collections of products, which may be custom and/or retail) containing particular vitamins, supplements, nutritional pills, powders, oils, diet supplements, liquid supplements, probiotics, hydration supplements, transdermal supplements, pills, capsules, oils, sprays, aerosols, fertility treatments, prenatal vitamins, and so on. These examples are not exhaustive; any suitable nutritional, dietary, or supplementation recommendation can be made in view of particular user goals (e.g., fitness goals, health goals, hair growth goals, body transformation goals, and so on).

In another example, the recommendation engine 200 can be configured to provide user-specific recommendation related to weight management and/or overall fitness. As with other embodiments described herein, the system can be configured to receive demographic and/or location information from a user to generate a listing of user-describing fingerprints/attributes such as described above, some of which may relate to a user's preference for or against particular methods of weight loss, weight gain, fitness routines/regimens, allergies to particular foods or goods, and so on. For example, some users may have a preference for cardio, whereas others maintain preferences for high impact interval training, class training, Pilates, yoga, and the like. Others still may have a preference for surgical weight management options. In these examples, as with others described herein, the recommendation engine 200 can be configured to instantiate a recommendation matrix correlating product/technique reviews of and/or including particular weight management techniques, methods, and/or service providers with user-describing fingerprints, such as described above. In this manner, the recommendation matrix can be leveraged to recommend to a user (or recommendations against) one or more techniques for weight management, one or more user-custom routines, and/or one or more consumer products relating to weight management such as weight-gain shakes, weight loss meal plans, and so on. These examples are not exhaustive; any suitable recommendation can be made in view of particular user goals and preferences, as described herein.

In another example, the recommendation engine 200 can be configured to provide user-specific recommendation related to holistic health and/or overall wellness. As with other embodiments described herein, the system can be configured to receive demographic and/or location information from a user to generate a listing of user-describing fingerprints/attributes such as described above, some of which may relate to a user's preference for or against particular products, items, foods, drinks, and so on. In these examples, as with others described herein, the recommendation engine 200 can be configured to instantiate a recommendation matrix correlating product/technique reviews that reference improvements to overall health or stress (e.g., product reviews that reference stress, sleep quality/duration, and so on) with user-describing fingerprints, such as described above. In this manner, the recommendation matrix can be leveraged to recommend to a user (or recommendations against) certain lifestyle changes (e.g., consuming less alcohol, smoking less, sleeping more, working out more, less sedentary lifestyle) along with product recommendations that reference overall improvements to wellness and so on. For example, a system may be configured to recommend a user reporting acne breakouts to buy a different pillow to improve sleep, to reduce drinking to increase sleep quality, to change pillow covers, to purchase or use a humidifier, and so on. These examples are not exhaustive; any suitable recommendation can be made in view of particular user goals and preferences, as described herein.

In another example, the recommendation engine 200 can be configured to provide user-specific recommendation related to holistic health and/or overall wellness. As with other embodiments described herein, the system can be configured to receive demographic and/or location information from a user to generate a listing of user-describing fingerprints/attributes such as described above, some of which may relate to a user's preference for or against particular products, items, foods, drinks, and so on. In these examples, as with others described herein, the recommendation engine 200 can be configured to instantiate a recommendation matrix correlating product/technique reviews that reference improvements to overall health or stress (e.g., product reviews that reference stress, sleep quality, and so on) with user-describing fingerprints, such as described above. In this manner, the recommendation matrix can be leveraged to recommend to a user (or recommendations against) certain lifestyle changes (e.g., consuming less alcohol, smoking less, sleeping more, working out more, less sedentary lifestyle) along with product recommendations that reference overall improvements to wellness and so on. For example, a system may be configured to recommend a user reporting acne breakouts to buy a different pillow to improve sleep, to reduce drinking to increase sleep quality, to change pillow covers, to purchase or use a humidifier, and so on. These examples are not exhaustive; any suitable recommendation can be made in view of particular user goals and preferences, as described herein.

In another example, the recommendation engine 200 can be configured to provide user-specific recommendation related to haircare, hair color, hair growth, and/or nail growth or care. As with other embodiments described herein, the system can be configured to receive demographic and/or location information from a user to generate a listing of user-describing fingerprints/attributes such as described above, some of which may relate to a user's preference for or against particular products, items, foods, drinks, and so on. In these examples, as with others described herein, the recommendation engine 200 can be configured to instantiate a recommendation matrix correlating product/technique reviews that reference particular hair and/or nail products with user-describing fingerprints, such as described above. In this manner, the recommendation matrix can be leveraged to recommend to a user (or recommendations against) custom products, custom ingredient mixtures, and/or retail products related to, but not limited to, hair growth, scalp care, shampoo, shampoo add-ins, conditioner, leave-in conditions, hair dye, facial hair care, facial hair oil, aftershave, shaving products, shaving devices, shaving electronics, hair removal electronics (e.g., depilators, at-home laser system, and so on), shaving tools, shaving oils, shaving foam, hair removal tools and products, and so on. These examples are not exhaustive; any suitable recommendation can be made in view of particular user goals and preferences, as described herein.

In another example, the recommendation engine 200 can be configured to provide user-specific recommendation related to fragrances, such as perfumes, colognes, room scents, candles, diffuser oils, and the like. As with other embodiments described herein, the system can be configured to receive demographic and/or location information from a user to generate a listing of user-describing fingerprints/attributes such as described above, some of which may relate to a user's preference for or against particular products, items, foods, drinks, and so on. In these examples, as with others described herein, the recommendation engine 200 can be configured to instantiate a recommendation matrix correlating product/technique reviews that reference particular fragrances, fragrance additives, delivery media (e.g., candle, incense, spray, aerosol, liquid, and so on) with user-describing fingerprints, such as described above. In this manner, the recommendation matrix can be leveraged to recommend to a user (or recommendations against) custom products, custom fragrances, custom ingredient mixtures, and/or retail products related to, but not limited to, sprays, aerosols, balms, candles, room fragrance, car fragrance, linen fragrance, clothing fragrance, fragrance to be added into other product categories, and so on. In some cases, fragrances may vary by product category and/or use case. For example, the recommendation matrix may recommend different fragrances for a user in the morning than in the evening. In other cases, a recommendation engine as described herein may be configured to provide recommendations of fragrance additives that cooperate together but are not identical. For example, a recommended perfume may be selected to complement a room fragrance, which in turn may be selected to complement a laundry fragrance. These examples are not exhaustive; any suitable recommendation can be made in view of particular user goals and preferences, as described herein.

In some further embodiments, the recommendation engine 200 can be configured to provide user-specific recommendation related to bath and body care. As with other embodiments described herein, such a system can be configured to receive demographic and/or location information from a user to generate a listing of user-describing fingerprints/attributes such as described above, some of which may relate to a user's preference for or against particular bath or body care products. For example, some users may have a preference for showering over bathing, or may have a preference for bath additives over post-bathing lotions and the like. In these examples, the recommendation engine 200 can be configured to instantiate a recommendation matrix correlating product reviews and/or including particular ingredients with user-describing fingerprints, such as described above. In this manner, the recommendation matrix can be leveraged to recommend to a user (or recommendations against) one or more ingredients, one or more user-custom products (or collections of products), and/or one or more consumer products (or collections of products, which may be custom and/or retail) packaged or intended for use as body wash, body lotion, oils, salts, bath bombs, body scrubs, and so on. These examples are not exhaustive.

In some further embodiments, the recommendation engine 200 can be configured to provide user-specific recommendation related to sexual wellness and sexual health. As with other embodiments described herein, such a system can be configured to receive demographic and/or location information from a user to generate a listing of user-describing fingerprints/attributes such as described above, some of which may relate to a user's preference for or against particular products, product types, ingredients, packaging material, disposability, and so on. In these examples, the recommendation engine 200 can be configured to instantiate a recommendation matrix correlating product reviews and/or including particular ingredients with user-describing fingerprints, such as described above. In this manner, the recommendation matrix can be leveraged to recommend to a user (or recommendations against) one or more ingredients, one or more user-custom products (or collections of products), and/or one or more consumer products (or collections of products, which may be custom and/or retail) packaged or intended for use as products relating to menstrual care, birth control, intimate care, personal lubricants, oils, sexual devices, nutritional supplements, erectile dysfunction, fertility support, and so on. These examples are not exhaustive.

In other examples, the recommendation engine 200 can be configured to provide user-specific recommendation related to medical or elective procedures and/or at-home treatments. As with other embodiments described herein, such a system can be configured to receive demographic and/or location information from a user to generate a listing of user-describing fingerprints/attributes such as described above, some of which may relate to a user's preference for or against particular aesthetics, treatment techniques, treatment types, and so on. In these examples, the recommendation engine 200 can be configured to instantiate a recommendation matrix correlating procedure/treatment reviews with user-describing fingerprints, such as described above. In this manner, the recommendation matrix can be leveraged to recommend to a user (or recommendations against), procedures and/or treatments or portions thereof such as but not limited to at-home beauty treatments and equipment, professional treatments and equipment, beauty procedures, treatments, elective or professional advised surgery (including injectables, such as botulinum toxin and derivatives thereof), laser treatments, plastic surgery, lights having therapeutic frequency ranges (e.g., infrared lights for localized heat, ultraviolet lights for tanning, and so on), and so on. In some cases, such recommendations may be made in view of one or more body dysmorphia risk assessments and/or diagnostic cues provided by a diagnostic matrix. In such examples, a system may recommend against elective procedures and/or treatment, and may instead advance recommendations related to positive body image reinforcement and/or pre-procedure counseling. These examples are not exhaustive; for example, in some cases over recommendation matrix may be further leveraged to provide recommendations types and/or methods of surgery, surgeon selection, practice/procedure credibility or risk, practice or practitioner experience, location, mental health inferences and interventions, and so on.

In still further embodiments, the recommendation engine 200 can be configured to provide user-specific recommendation related to color cosmetics and/or makeup. In particular, as with other embodiments described herein, the system can be configured to receive demographic and/or location information from a user to generate a listing of user-describing fingerprints/attributes such as described above, some of which may relate to a user's preference for or against particular products, product types, finishes, price ranges, ingredient origin, and so on. For example, some users may have a preference for liquid liners, powder foundation and so on. In other cases, certain users may have particular preferences for particular colors or color additives/properties (e.g., shimmer, glint, matte, and so on). In these examples, the recommendation engine 200 can be configured to instantiate a recommendation matrix correlating product reviews and/or including particular attributes or properties with user-describing fingerprints, such as described above. In this manner, the recommendation matrix can be leveraged to recommend to a user (or recommendations against) one or more ingredients, one or more user-custom products (or collections of products), and/or one or more consumer products (or collections of products, which may be custom and/or retail) containing or intended to be used as lipstick, eye color, brow care, eye liner, blush, lip liner, polishes, aesthetic applications onto a person, and so on. These examples are not exhaustive.

In still further embodiments, the recommendation engine 200 can be configured to provide other user-specific recommendations. For example, the recommendation engine 200 can be configured to provide user-specific recommendation related to mental health, physical fitness, addiction care, diet, and/or oral health. In particular, as with other embodiments described herein, the system can be configured to receive demographic and/or location information from a user to generate a listing of user-describing fingerprints/attributes such as described above, some of which may relate to a user's preference for or against particular products, exercises, therapies, dentists, and so on, and so on. In these examples, the recommendation engine 200 can be configured to instantiate a recommendation matrix correlating product reviews and/or including particular attributes or properties with user-describing fingerprints, such as described above. In this manner, the recommendation matrix can be leveraged to recommend to a user (or recommendations against) one or more ingredients, one or more user-custom products (or collections of products), and/or one or more consumer products (or collections of products, which may be custom and/or retail) containing or intended to be used as, without limitation: foods from a nutrition perspective and taste preference perspective; potential allergens; potential overall health or wellness antagonists that may not be allergy antagonists (e.g., reducing gluten or lactose or sugars); types of exercise, equipment, environment, smart device, based on heath, preference, mental health, lifestyle, smart machines, and so on; toothpaste, toothbrushes, dental care, teeth whitening, mouth rinse, periodontal care, and so on; mental health advancing therapies, treatments, mitigating modalities (specific to a particular user, such as high-stress work life, and so on), tools, lifestyle changes, type of therapy or therapy technique to seek, specific therapist, and so on.

In still further examples, a recommendation matrix can be leveraged to provide overall quality of life improvements. For example, leveraging information related to a user complaint of dry skin can result in a recommendation that a user change hair conditioner (as the user's hair may also be dry), that the user move to a higher humidity environment, that the user invest in a whole-home humidifier, that the user adopt use of a CPAP humidifier machine, that the user reduce temperature of showers, that the user increase intake of certain nutrients, that the user decrease intake of certain nutrients and so on. In other cases, the recommendation matrix may be configured to recommend specialized products to a user such as side-sleep pillows, specialized mattresses, sound machines for sleep, heating pads, cooling pads, and so on.

These foregoing embodiments are not exhaustive of the various use cases of a recommendation matrix as described herein. More generally and broadly, it may be appreciated that by fingerprinting certain demographic information as described above, along with location information and environment information, against properties of products—and not the products themselves—and/or properties of regiments, techniques, methods, and so on, a system as described herein can provide recommendation beyond a set of commercially available products or techniques available at a particular time, or in a particular area.

Further, recommendations as described herein can be varied based on environment, season, weather, and so on. Two demographically similar persons living in different environments may receive different recommendations. Two demographically different persons living in different environments with different preferences or personal care goals may receive the same recommendations.

In some cases, a system as described herein can be used on an on-going basis to provide recommendations that vary with time, season, or location. For example, if a user of a system as described herein is considering moving from a first location to another location, the system can be configured to provide a recommendation or analysis of which location may be associated with an overall increase in quality of life. For example, if a user living in the American southwest has an ongoing complaint of dryness in hair, skin, and so on is considering a move to the pacific northwest or the northeast, as system as described herein may be leveraged to recommend to the user to prefer the pacific northwest, as humidity improvements without corresponding large temperature swings, may benefit the user's skin and hair to a greater extent than if that same user moves to the northeast.

In other examples, a system as described herein can be leveraged to create customized products for a user that can be varied based on an upcoming event, such as an upcoming seasonal change or an expected travel plan of a particular user. For example, a user of a custom-ingredient mixture skincare product when at home may be provided with a different mixture when the user travels to a different climate for a vacation.

These foregoing example embodiments are also not exhaustive of the recommendation matrix as described herein. For example, in some cases, a recommendation matrix that correlates extracted attributes from product reviews (some or all of demographic attributes, location attributes, product attributes, and attributes describing how that product was used by a particular reviewer) to direct attributes of a user can be used for other purposes. For example, a recommendation matrix can be used to provide recommendations related to children, toddlers, babies, and pets.

Relating to children (and/or early motherhood, fatherhood, guardianship and parenthood), examples include recommendations may relate to to health, toys, dental care, vitamins, supplements, prenatal care, postpartum care, breastfeeding care, skincare, formula, electrolyte solutions, diapering, in-home hazard identification (e.g., lead testing, baby-proofing)

Relating to pets, examples include recommendations related to pet health (e.g., nutrition/supplementation, cannabidiol, powders, anti-anxiety, dental care, periodontal care, and so on), pet food (e.g., based on type, breed, age, weight, and so on), pet toys (e.g., based on activity level, breed, size, other pets, presence of children, pet implied loneliness based on owner or playmate availability, and so on), pet training, pet lodging, pet selection (e.g., which pet to select based on life, lifestyle, mobility, preferences, environment, living environment, house size, family members, social connections, and so on).

As noted above, these foregoing example embodiments and example uses cases of a recommendation matrix as described herein are not exhaustive; a person of skill in the art may readily appreciate that a recommendation matrix based on correlations between personal attributes and product attributes can be leveraged for a litany of purposes, including the skincare examples that follow, provided for simplicity and brevity of description.

Figure 2B:
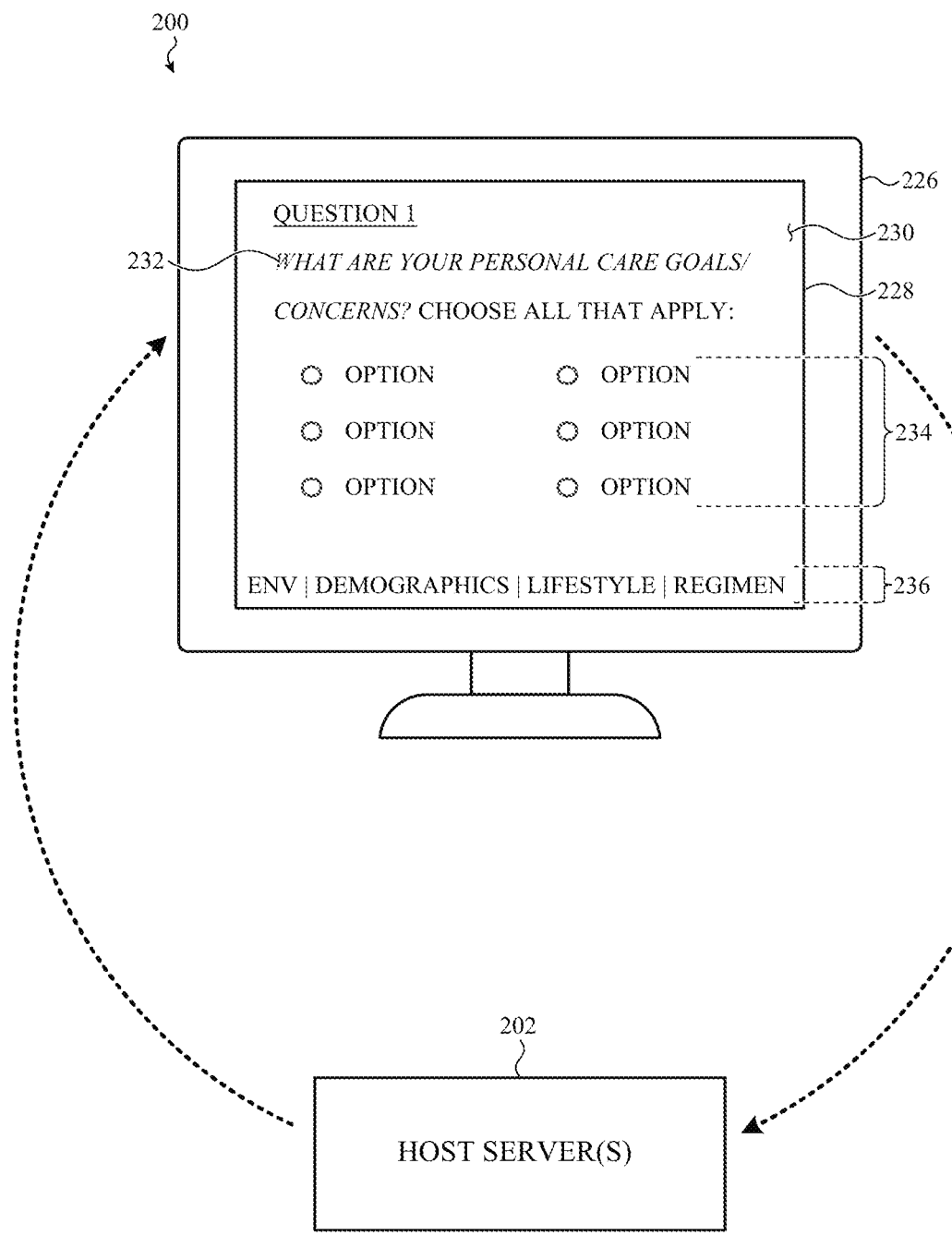
FIG. 2B illustrates an example of a signal/process flow diagram depicting a client device in communication with a system, as described herein.

FIG. 2B is a signal/process flow diagram depicting a client device in communication with the host server of FIG. 1 and rendering a graphical user interface configured to solicit input from a user of the client device so that the host server can provide a recommendation to that user. In particular, in this embodiment, the recommendation engine 200 includes a host service 202, for example, a skincare system, in communication with a client device 226. The client device 226 includes a display 228 that renders a graphical user interface 230.

In this example, the graphical user interface 230 renders a portion of a questionnaire that can be served to the client device 226 to solicit user information from a user operating the client device 226. In this embodiment, the graphical user interface 230 can present a question 232 to the user. In response to the question 232, the user may select one or more options, such as the options 324 to provide demographic information to the host service 202 such that the host service 202 can provide a recommendation for a skincare product to the user. The question(s) asked of the user by the host service 202 can thematically vary (see, e.g., the questionnaire sections 236). For example, as depicted in FIG. 2, questions can be asked of the user related to the user's skin concern and/or concerns, user demographics, user lifestyle (e.g., activity level, outdoor activity, swimming activity, and so on), user skincare regimen, and so on.

Figure 3:
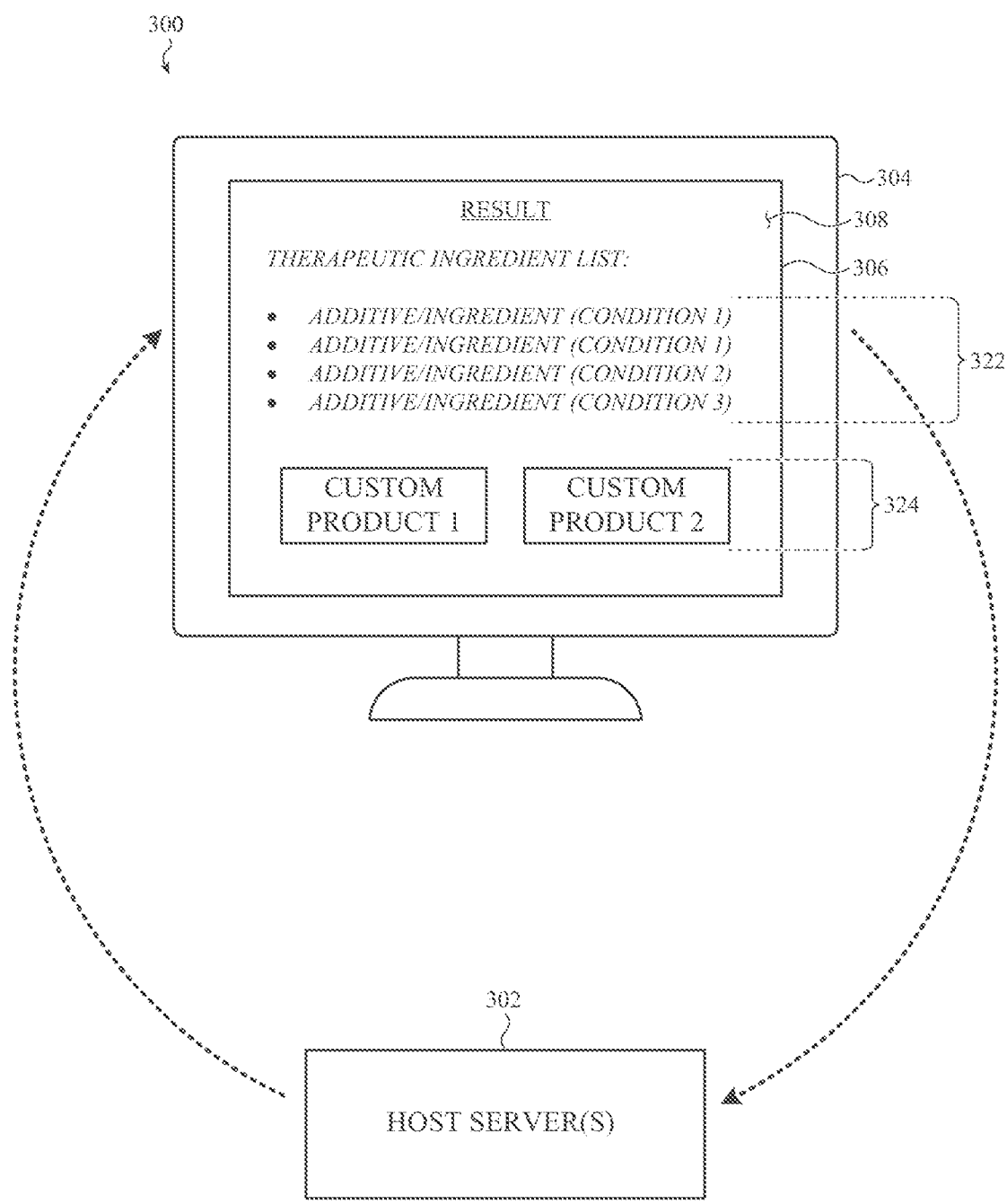
FIG. 3 illustrates an example of a signal/process flow diagram depicting a client device in communication with a system, as described herein.

The recommendation engine 300 of FIG. 3 can be configured to provide one or more recommendations to the user. FIG. 3 is a signal/process flow diagram depicting the client device of FIG. 1 rendering a graphical user interface presenting one or more product recommendations to the user of the client device. In this embodiment, the host server 302 instructs the client device 304 to display, via the display 306 and the graphical user interface 308, a set of recommendations 322 for the user. In some embodiments, the user may be further presented with an option to purchase a customized product by selecting a custom product 324.

Figure 4:
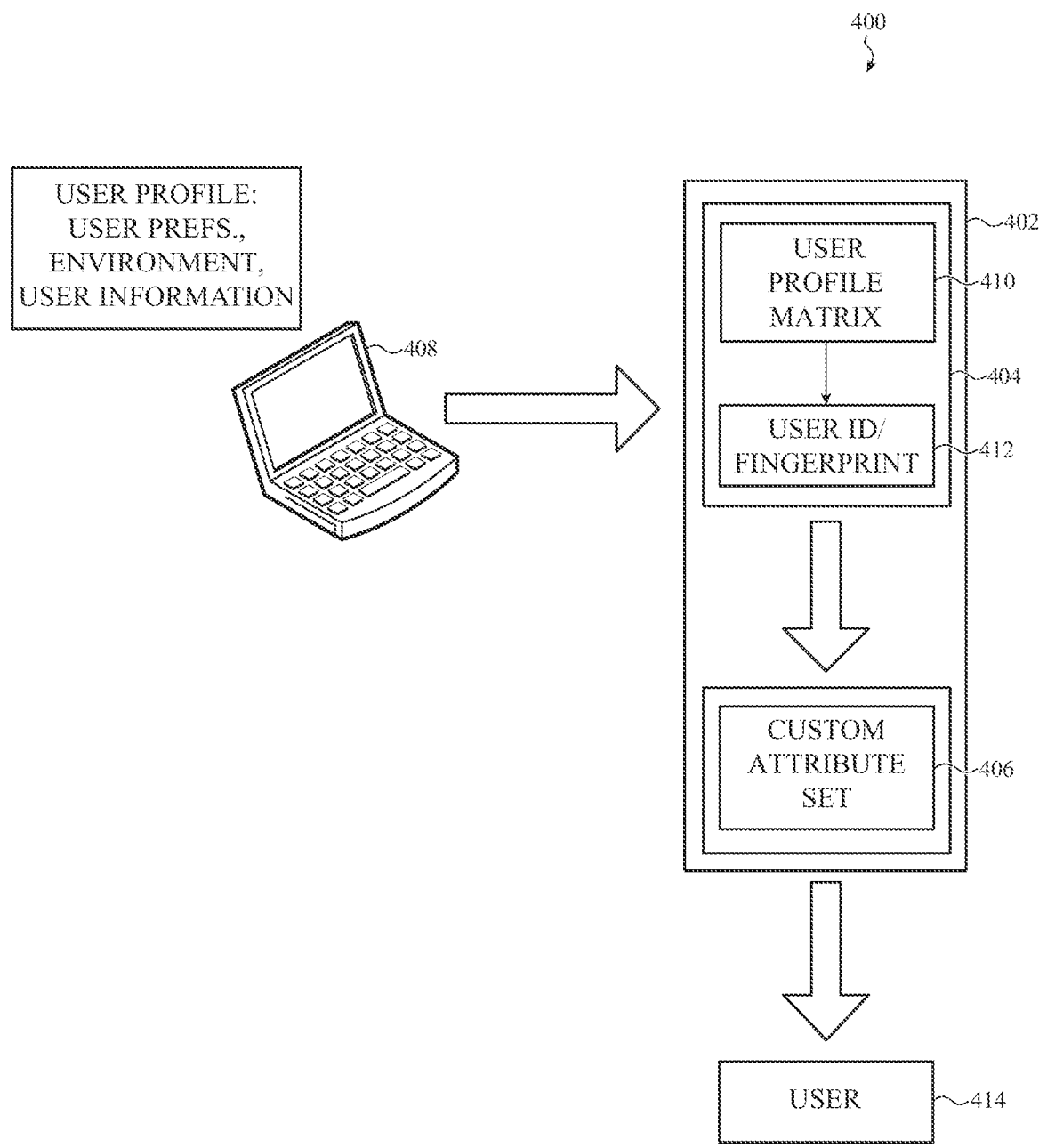
FIG. 4 illustrates an example of a recommendation system data flow process.

FIG. 4 illustrates an example of a recommendation data flow process 400, which may include a recommendation system 402. In some examples, the recommendation system 402 may be configured to receive, process, output, and transmit various types of data which may be skincare related or non-skincare related. In the example of FIG. 4, the recommendation system 402 may facilitate receiving user data by a processing block of the recommendation system 402. The processing block 404 of the recommendation system 402 may receive the user data and may prepare a custom recommended attribute set 406 which may be provided to a user. In some examples, the processing block may be a processor with a database service configured to translate, correlate, and/or select data in the recommendation system 402. The recommendation system 402 may or may not include an input device such as a laptop, desktop, mobile device, smart phone, tablet, and so forth. The term input device may be used interchangeably with client device. Additionally, the one or more fingerprints related to the user processing performed by the recommendation system 402 may occur at the same or different location as the skincare data input by the user.

Generally and as illustrated in FIG. 4, the recommendation data flow process 400 may include an input device 408. The input device 408 may be configured to provide the user with a dynamic questionnaire, for example, via an application or a website. The user-describing demographic data, preference data, and/or user personal care goal data entered at the input device 408 may be provided to the recommendation system 402. The recommendation system 402 may be provide, via the processing block 404, a one or more fingerprints related to the user (not illustrated in FIG. 4) which may be documented by employing a user profile matrix 410. The skin profile matrix 420, via the processing block 404, may then be translated into a user-describing fingerprint(s) 412, which may be a string of characters, where the characters may be representative of different one or more fingerprints related to the user factors. The processing block 404 may include a user profile matrix 410 which may be used in conjunction with the user-describing demographic data, preference data, and/or user personal care goal data to generate a user skin identifier 412. The user-describing fingerprint(s) 412 may then be used, via the processing block 404, to select a custom recommended attribute set 406 for the user 414. In some examples, the processing block 404 may operate in the environment of the host server as discussed with reference to FIGS. 4-9.

In FIG. 4, the input device 408 may be employed by the user to enter the user-describing demographic data, preference data, and/or user personal care goal data. The input device 408 may be any appropriate computing device such as a laptop computer, a desktop computer, any type of mobile device, a smart phone, a tablet, and so forth.

The user may enter the user-describing demographic data, preference data, and/or user personal care goal data on the input device 408 via a website, application, or any other appropriate data entry system and the user-describing demographic data, preference data, and/or user personal care goal data may be entered on the input device 408 which may be located in retail stores, via any type of personal computing and/or mobile device, or at a facility associated with the product vendor. Although the input device 408 is depicted in FIG. 4 in a different location than the user, the illustration in FIG. 4 is for discussion purposes. In some examples, the user may be in the same location as the input device 408.

The user may input information which may include user-describing properties/attributes and/or non-user-describing properties/attributes. User-describing properties/attributes may include, in a skincare context, skin issues and/or skin concerns which may be indicated by the user when entering the user-describing demographic data, preference data, and/or user personal care goal data.

Skin issues and skin concerns may include, for example, oil production of the user's skin, allergies to ingredients, specific skin issues such as rosacea, acne, eczema, hyperpigmentation, fine lines, dark circles under the eyes, premature wrinkles, puffy eyes, crepey skin, any combination thereof, and so forth.

Non-user-describing properties/attributes may include user traits that may not be identified by the user as skin concerns. In some examples, non-user-describing properties/attributes may include information regarding the geographic region that the user resides, water intake, activity level, sun exposure, pollution levels, water hardness, activity level, hydration level, gender, hours spent using electronic devices, stress level, hours of sleep, preferences, allergies, goals, methods used in the past, methods rejected, methods that have worked, and so on, any combination thereof, and so forth.

The non-skin related information may still affect a user's skin, but may be general information of the user such as location, hours of sleep, hours of activity, and so forth. The user-describing properties/attributes and non-user-describing properties/attributes are listed as possible examples of the type of data the user may enter, but may include any appropriate data that is skin-related or non-skin related. Non-user-describing properties/attributes may include known dynamic factors or anticipated changes, such as seasonal and temperature changes which may affect the ingredients of the curated product portfolio.

These anticipated changes and how they affect the ingredients of the products will be discussed in further detail in at least FIGS. 2A-2B and 3. Though the data to be entered is discussed herein as a list of factors, the data to be entered may be dynamically selected based on the user responses as will be discussed in further detail herein in FIGS. 4-9.

In some examples of FIG. 4, the input device may provide the dynamic questionnaire to the user and the dynamic questionnaire may ask the user questions in an order and with content specific to the user answering those questions. The dynamic questionnaire may be configured to present follow-up questions, to omit irrelevant questions (as determined by user input, user demographics, and/or answers to previously-presented questions), to ask supplemental questions, and so on. The user input of the dynamic questionnaire may provide the recommendation system 402 with the user-describing demographic data, preference data, and/or user personal care goal data.

After the user-describing demographic data, preference data, and/or user personal care goal data is entered by a user on the input device 408, the user-describing demographic data, preference data, and/or user personal care goal data may be transmitted to the recommendation system 402. The recommendation system 402 may receive the user-describing demographic data, preference data, and/or user personal care goal data which may include user skincare information and general user information that may or may not include specific skin information. The user-describing demographic data, preference data, and/or user personal care goal data received by the recommendation system 402 may be used to generate a one or more fingerprints related to the user.

The one or more fingerprints related to the user may be an entry in a recommendation system 402 database or in some examples may be an entry in a client or customer database. In some examples, a diagnosis of one or more skin concerns presented by the user may be determined by leveraging a predictive model trained by information obtained from at least customer review data scraped from a public resource, a user-specific ingredient list may be determined by leveraging a predictive model trained by information obtained from at least customer review data scraped from a public resource. The one or more fingerprints related to the user may be documented in the form of a user profile matrix. The user profile matrix may be a multidimensional matrix, in that different data points of the user's associated fingerprint(s) (e.g., demographic fingerprints, geographic fingerprints, preference fingerprints, and the like) may indicate an intersection or correlation of two, three, or more attributes/properties or other factors. The user profile matrix will be discussed in further detail in at least FIGS. 4-6.

The recommendation system 402 may be a platform that supports real time or near real time processing of using the user's associated fingerprint(s) 412 to select the ingredients for the products of the curated product portfolio. The user's associated fingerprint(s) may be a concatenated string of characters, each of which may represent different user skin care factors from the user profile matrix 410. Individual factors of the user profile matrix may be assigned to a representative character to create or derive the user's associated fingerprint(s) 412.

The user's associated fingerprint(s) may include information to create and/or select the custom recommended attribute set 406. Additionally, in some examples, a user-specific ingredient list may be determined by leveraging a predictive model trained by information obtained from at least customer review data scraped from a public resource. The custom recommended attribute set 406 may be one or more skincare products, such as, a facial cleanser; a topical sunscreen; a topical serum; an exfoliator; a moisturizer; a chemical peel; a toner; an eye cream; a night cream; or any combination thereof, and so forth. Each of these products of the curated product portfolio may have individually selected ingredients based specifically on the one or more fingerprints related to the user.

The custom recommended attribute set 406 may be provided as a recommendation to the user 414 and the user 414 may review the recommended custom recommended attribute set 406 soon after entering the user-describing demographic data, preference data, and/or user personal care goal data on the input device 408. In some examples, the recommended custom recommended attribute set 406 may be provided to the user in real-time, after the user enters the user-describing demographic data, preference data, and/or user personal care goal data. The user 430 may review each product of the custom recommended attribute set 406 and may review the ingredients of each product. In addition to each of the individual products of the curated product portfolio, a corresponding list of skin issues and/or concerns may be provided for each product and the corresponding list of skin issues may be generated from the initial user profile. Each of the lists that correspond to a product of the curated product portfolio may inform the user which of the concerns are addressed by the individually formulated product. The curated product portfolio and individually formulated products will be discussed in further detail herein with respect to at least FIGS. 4-6.

The custom recommended attribute set 406 may be recommended to the user 414 via the input device 408 or any other computing device from which the user 430 may access the custom recommended attribute set 406 and the user 414 may review the individual products, the custom recommended attribute set 406, the ingredients in each of the individually formulated products, and the skin concerns and/or issues that each product may address. The recommendation system 402 may be capable of approximately real-time rendering and the product portfolio recommendations and/or results may be accessible by the user after the user enters the user skin data.

The curated product portfolio or the individual products of the curated product portfolio may be provided to the user 430 for purchase. The user 430 may choose to wait on the purchasing decision, may purchase individual products or may purchase the custom recommended attribute set 406. In some examples, the recommendation system 402 may include a facility to manufacture the individualized products. In other examples, the individualized products may not be manufactured by a facility that is part of the recommendation system 402.

The recommendation system 402 may provide a recommended curated product portfolio to the user 414. Although in FIG. 4, the user 414 may be depicted at a different location than the input device 408, the user may receive the individualized recommendation at the input device 408 in real-time after entering the requested user-describing demographic data, preference data, and/or user personal care goal data. In some examples, the user 414 may access the recommended curated product portfolio at a later time and/or on a different device, as the user 414 may review the curated product portfolio from any computing device and/or mobile device.

The recommendation system 402 may provide the individual products or the entire curated product portfolio to the user 414 for purchase and/or automatic reorder. Additionally, the user 414 may opt to purchase the product or products immediately or in the future. In some examples, the automatic reorder may provide an automatically updated product portfolio which will be discussed in further detail herein. In some examples, the custom recommended attribute set 406 may be one or more products, and in one example the custom recommended attribute set 406 may be three separate products. In some examples, the three separate products of the custom recommended attribute set 406 may be a cleanser, a sunscreen day cream, and a night cream.

Figure 5:
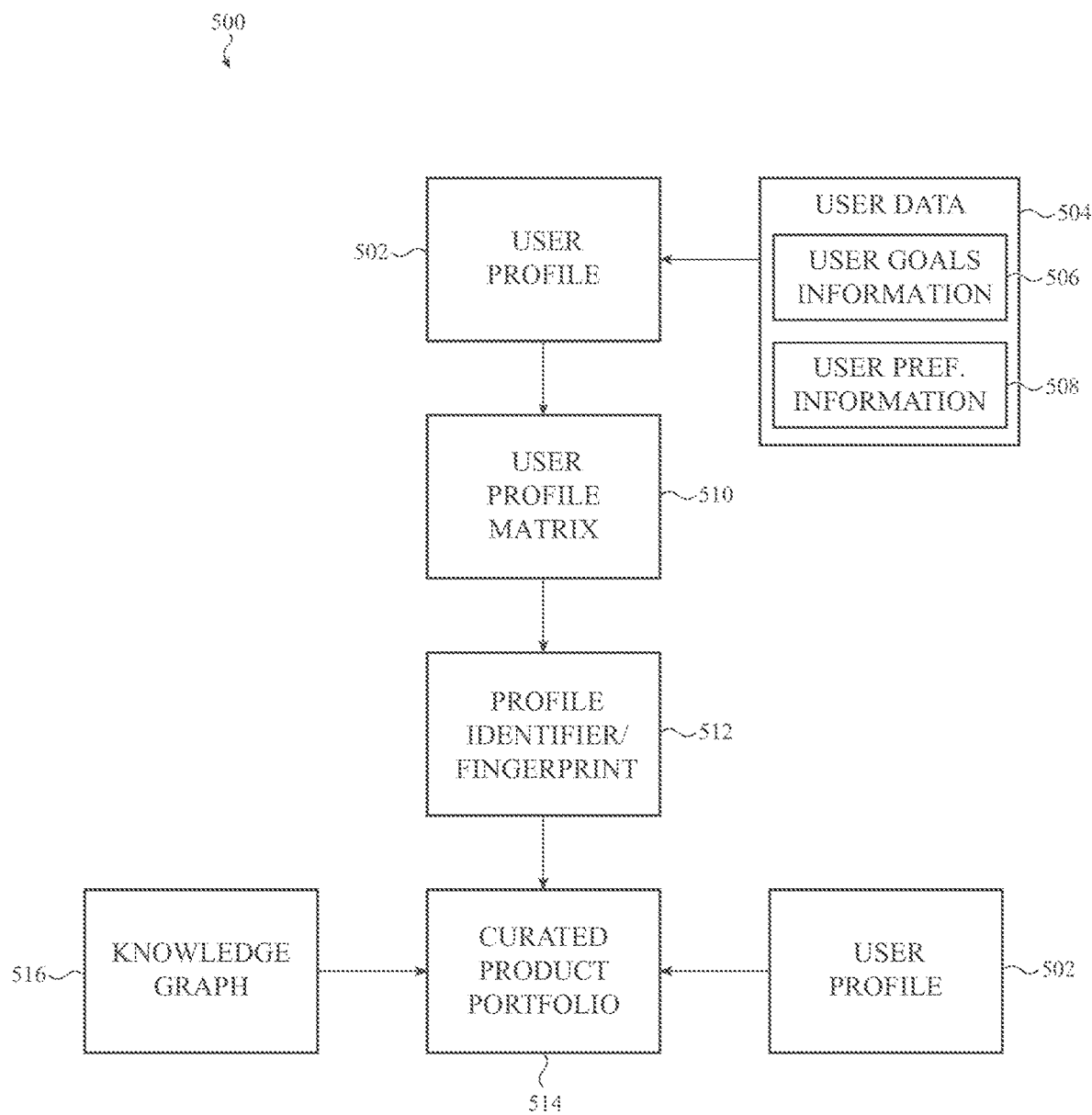
FIG. 5 illustrates an example of a personalization platform for providing a recommendation, such as described herein.

FIG. 5 illustrates an example of a personalization platform 500 of providing a skincare product recommendation. In the example of FIG. 5, the personalization platform 500 may include receiving user-describing demographic data, preference data, and/or user personal care goal data which may be skincare related data or non-skincare related data and generating a user skincare profile. The user skincare profile may be used to select, prepare, and provide a curated product portfolio to the user. The personalization platform 500 may or may not include an input device such as a laptop, desktop, mobile device, smart phone, tablet, and so forth. Additionally, the processing which may be performed by the personalization platform 500 may occur at the same or different location as the skincare data input by the user.

As illustrated in FIG. 5, the one or more fingerprints related to the user 502 may be generated from received user data 504 which may include user goal information 506 and user preference information 508. The user data 504 may be the raw data which is entered by the user as discussed with respect to FIG. 1. In some examples, the one or more fingerprints related to the user 502 may be included in a skincare database, which may include appropriate data formatting and database identifiers. In some examples, a diagnosis of one or more skin concerns presented by the user may be determined by leveraging a predictive model trained by information obtained from at least customer review data scraped from a public resource. The diagnosis determined by the predictive model may also be included in the one or more fingerprints related to the user 502. The one or more fingerprints related to the user 502 may be documented in a user profile matrix 510.

User profile matrix 510 may organize the user data 504, which may include two types of information, a first type which may be user goal information 506 and user preference information 508. The goal information 515 may include, in examples related to skincare, skin issues and/or skin concerns identified by the user.

The user information may include information, in a skincare related context, that is non-skin related information such as general information regarding the user and the user's lifestyle. The user information may include at least: the location of the user; water intake; activity level; sun exposure; pollution levels; water hardness; activity level; hydration level; gender; hours spent using electronic devices; stress level; hours of sleep; ethnicity; or any combination thereof; and so forth. The user-describing properties/attributes and non-user-describing properties/attributes are listed as possible examples of the type of data the user may enter, and may include any additional appropriate data that is skin-related or non-skin related.

User profile matrix 510 may include user-specific attributes which may be organized into two or more dimensions. In some examples, there may be a greater number of user-specific attributes than user data factors. For example, user data 504 may include the user's geographic location, but the user-specific attributes may include various types of information about the user's geographic location. For example, pollution levels, water hardness, UV exposure, humidity, temperature, allergen information for native grasses, trees, molds, flowers, and so forth, may all be user-specific attributes that correspond to the user's geographic location. User profile matrix 510 may automatically account for the additional corresponding data for user-specific attributes which may be associated with the user data 504.

The user-specific attributes of the user profile matrix may have individual representative markers associated with and corresponding to each user-specific preference-related and/or goal-related attribute. In one example, a user-specific preference-related and/or goal-related attribute may have varying degrees and each of these varying degrees of the user-specific preference-related and/or goal-related attribute may have an associated individual representative marker.

For example, UV exposure may have five different representative markers associated with it which may correspond to five different levels of UV exposure. In some examples, very low UV exposure may have a first representative marker, low UV exposure may have a second representative marker, average UV exposure may have a third representative marker, high UV exposure may have a fourth representative marker, and very high UV exposure may have a fifth representative marker. These representative markers may be used in the skin user identifier discussed herein and at least in the discussion of FIG. 5.

Additionally, in some examples, the user profile matrix may be a multidimensional matrix, in that different data points of the user's associated fingerprint(s) may indicate an intersection or correlation of two, three, or more skincare factors. For example, a user's associated fingerprint(s) may include the correlated or intersecting skincare factors of being 19 years old, having oily skin, and living in a high humidity climate. Although each of these factors may be accounted for individually in multiple skincare products, when the intersecting skincare factors are simultaneously accounted for, a more effective skincare recommendation and product or product line may be provided to the user.

The one or more fingerprints related to the user 502 may be documented in the user profile matrix 510 at the level of the user-specific attributes and the corresponding individual representative markers. After the user data 504 is received and the one or more fingerprints related to the user 502 is generated, the individual elements or factors of the one or more fingerprints related to the user 502 may be mapped to the user-specific attributes to produce the user profile matrix 510. In some examples, each individual element or trait of the one or more fingerprints related to the user 502 may be matched or mapped to the appropriate corresponding user-specific preference-related and/or goal-related attribute(s) in the user profile matrix 510.

For example, a one or more fingerprints related to the user 502 may include a user location in New Orleans which may correspond to a number of user-specific attributes including, among other factors, humidity levels. The one or more fingerprints related to the user 502 user location, may map to a corresponding user-specific preference-related and/or goal-related attribute of a very high level of humidity. Further, there may be an individual representative marker which may correspond to the user-specific preference-related and/or goal-related attribute of a very high level of humidity.

The user-specific attributes and accordingly, the user profile matrix 510 may be dynamic and may change according to any relevant information. For example, in the future, a user-specific preference-related and/or goal-related attribute may change such as the season or temperature. Because this change alters the user-specific preference-related and/or goal-related attribute, the user profile matrix 510 changes as well. Additionally, this changing factor may interact with other user-specific attributes, thus further altering the user profile matrix 510.

The user's associated fingerprint(s) 512 may be derived from the user profile matrix 510. As previously discussed, the user profile matrix 510 may have individual representative markers for each of the user-specific attributes. In some examples, the user's associated fingerprint(s) 512 may be a concatenated string of individual representative markers from the user profile matrix 510. Although the user's associated fingerprint(s) may be any number of characters, in some examples, the user's associated fingerprint(s) 512 may be 58 characters long and these characters may be used to select the ingredients in one or more custom products.

The selection of the ingredients may additionally be based on the highest likelihood of achieving the best results for the user. Furthermore, in some examples, a user-specific ingredient list may be determined by leveraging a predictive model trained by information obtained from at least customer review data scraped from a public resource. As such, in some examples, the curated ingredient list may be determined using both the predictive model and the user's associated fingerprint(s) 512.

In some examples, the user's associated fingerprint(s) 512 may differ from the one or more fingerprints related to the user 502 and the user data 504. As previously discussed, the user data 504 may be the raw data entered by the user and the one or more fingerprints related to the user 502 may be generated by the skincare system which may include a database service and the one or more fingerprints related to the user 502 may be an entry in a user database.

The user's associated fingerprint(s) 512 may include a string of characters which correspond to individual representative markers. The individual representative markers may be unique identifiers that correspond to user-specific attributes included in the user profile matrix 510. In some examples, the characters of the user's associated fingerprint(s) may be either representative of a skin-related factor such as dry skin or a non-skin related factor such as the humidity level. The user's associated fingerprint(s) 512 may, at a high level, be used to map the one or more fingerprints related to the user 502 to base ingredients and additives for formulating the product portfolio for the user. By using this personalization skincare platform, the products of the product portfolio are individualized and curated products for the user.

In some examples, the user's associated fingerprint(s) 512 may be updated or may change according to anticipated changes to the one or more fingerprints related to the user 502. The skincare system may include the dynamic and automated ability to generate an updated one or more fingerprints related to the user based on existing user data which may be dynamic, for example seasons associated with a user's location. The one or more fingerprints related to the user and the user profile matrix may be automatically updated when existing user data includes anticipated changes in the user information.

Accordingly, the user's associated fingerprint(s) 512 may be updated based on the anticipated change associated with the one or more fingerprints related to the user. In some examples, the one or more fingerprints related to the user 502 may not change and the user's associated fingerprint(s) may be updated based on a trigger which will be discussed in further detail herein. Because the user's associated fingerprint(s) 512 may be updated, the curated product portfolio 514 may also be altered and the updated products may be recommended to the user, provided to the user for purchase, or automatically sent to the user.

Anticipated changes may be built into the user's associated fingerprint(s) and may be triggered or signaled by various factors. In this example, there may not be a change or update to the one or more fingerprints related to the user 502 even though the user's associated fingerprint(s) 512 may be updated. In some examples, the anticipated change to the user's associated fingerprint(s) may be triggered by the time of year which may indicate a change in season and accordingly a temperature change depending on the geographic location of the user. For example, the user data 504 and the one or more fingerprints related to the user 502 may indicate that the user location is in Minnesota where the seasons change and there are significant variations in the temperature. As the temperature changes, the user's associated fingerprint(s) 512 may be updated which may affect the selection of the product ingredients. The curated product portfolio 514 may be updated based on the anticipated change or changes.

The curated product portfolio 514 may be selected based at least partially on the user's associated fingerprint(s) 512 and the knowledge graph 516. The knowledge graph 516 may include information regarding the effectiveness of the base ingredients and additives which may be selected to formulate the curated product portfolio 514, as well as interactions between the base ingredients and additives. The products may include one or more base ingredients and one or more additives. The base ingredient may be a relatively benign carrier base or foundation into which the active ingredients or additives may be added.

The knowledge graph 516 may effectively and accurately match the user's associated fingerprint(s) to the appropriate ingredients that may address the user's skin issues and may provide the highest likelihood of success by addressing and/or improving the user's skin issues. Using the knowledge graph 516 and the user's associated fingerprint(s) 512, base ingredients and additives may be selected for each of the products of the curated product portfolio 514. Selecting the base ingredients and additives based on the user's associated fingerprint(s) and knowledge graph may provide a highly individualized and specific ingredient set (in the case of skincare product recommendations) and/or attribute set that can be used to create a custom product portfolio to the client since there are at least hundreds of thousands of available combinations.

Further, in some examples, one or more additives may be selected and combined together, and even though the additives may interact with one another, this interaction may be accounted for when formulating the curated product portfolio. In some examples, combining certain base ingredient and additive combinations may be more or less effective for different factors such as varying levels of humidity or gender and the efficacy of the combinations in different environmental conditions and other varying conditions may be accounted for and addressed while selecting ingredients.

Each product of the curated product portfolio 514 may have one or more lists associated with each of the products. In some examples, the active ingredients may be listed and if desired the full ingredient list, including relatively benign ingredients, may also be accessed and reviewed by the user. In some examples, each of the products may include a list of concerns which the product may address. The concerns may correspond to skin issues or concerns that the user indicated when entering the initial user data 504.

In some examples, the curated product portfolio 514 may include three products. Each product may address a different skin issue or two or more products may address the same skin issue indicated by the user. Each product may include different ingredients than the other products, but even though the ingredients may be different product to product, each product may include complementary ingredients to the ingredients of the other products. The products may available for individual purchase by the client or may be available for purchase as a curated product portfolio or product set. In some examples, the clients may automatically receive the curated product set after a predetermined time interval, such as every two months.

FIG. 6 illustrates an example skincare matrix 600. In some examples, the matrix 600 depicted in FIG. 6 may be configured to logically provide a mapping to a one or more fingerprints related to the user. In the example of FIG. 6, the matrix 600 may include at least multiple rows and columns of user-specific attributes. The matrix may be used to correlate the one or more fingerprints related to the user to the user-specific attributes and the matrix may be used to generate a user's associated fingerprint(s) which may be used to select, prepare, and provide a curated product portfolio to the user.

By way of example and for purposes of description, the matrix 600 may be a set number of rows and columns of user-specific attributes for discussion purposes only, and in practice may be any appropriate number of rows and columns. The user-specific attributes of FIG. 6 are organized in the matrix 600 and may be similar to the user-specific attributes as discussed with reference to FIGS. 4 and 5. The matrix 600 may be used for to generate a user's associated fingerprint(s).

As illustrated in FIG. 6, the matrix 600 may include rows and columns of various user-specific attributes. The user-specific attributes may include any relevant factor that may affect the skin and/or skin concerns of the user. In some examples of FIG. 6, the columns may be different user-specific attributes and may include skin-related information and non-skin related information. As previously discussed, the non-skin related information may still affect a user's skin, but may be general information of the user such as location, hours of sleep, hours of activity, and so forth.

The columns may include factors such as hyperpigmentation, fine lines, and eczema, and may also include other factors such as ethnicity, gender, age, UV exposure, and water hardness. In some examples of FIG. 6, the rows may be varying degrees of the user-specific attributes listed in the columns. For example, matrix factor x1 may be UV exposure and matrix factors y1 through y5 may be the degree of UV exposure. In some examples, matrix factor y1 may be very low UV exposure, matrix factor y2 may be low UV exposure, matrix y3 may be average UV exposure, matrix factor y4 may be high UV exposure, and matrix factor y5 may be very high UV exposure.

Although each column may be different, the rows may still be varying degrees of the column user-specific attributes. For example, the column may be humidity and the rows may be varying degrees of very low to very high which may correlate to the column humidity. In still further examples, the column may be sensitive skin and the rows may include varying degrees of the skin sensitivity of the user or vice versa. In some examples, the rows and columns may both include user-specific attributes including skin-related factors and non-skin related factors.

In FIG. 6, the user profile matrix 600 includes examples of alpha numeric individual representative markers A11, B22, C35, and D43. These individual representative marks are provided for discussion purposes only and may be any type of identifier that is representative of the user's skin information and general information. An individual representative marker may be one character or multiple characters as appropriate. In FIG. 6, the individual representative marker may provide information of the user-specific preference-related and/or goal-related attribute x1 which may be sensitive skin.

Because the individual representative marker is A11, this may indicate that the user has sensitive skin, but that the sensitive skin is low level, which is indicated by the second one. In the example, the user does not have sensitive skin, the individual representative marker may be A00 which may indicate that A represents sensitive skin, but the zeros indicate that the user does not have sensitive skin. The individual representative marker C35 may indicate that the user lives in a very high level humidity area, where the user-specific preference-related and/or goal-related attribute x3 may be humidity level. In this example, the individual representative markers may be concatenated to form the user's associated fingerprint(s). Additionally, in this example, the user's associated fingerprint(s) may have four concatenated individual representative markers, but may be any appropriate number of concatenated markers.

The matrix 600 may be a multidimensional matrix beyond being a two dimensional, rows and columns, matrix. The matrix 600 may be a multidimensional matrix, in that different data points of the user's associated fingerprint(s) may indicate an intersection or correlation of two, three, or more skincare factors. For example, a user's associated fingerprint(s) may include the correlated or intersecting skincare factors of being 19 years old, having oily skin, and living in a high humidity climate. Although each of these factors may be accounted for individually in multiple skincare products, when the intersecting skincare factors are simultaneously accounted for, a more effective skincare recommendation and product or product line may be provided to the user.

In some examples, the user-specific attributes may interact with one another. For example, if a first user has dry skin and lives in a location with high UV exposure and a second user has oily skin and lives in the same location with high UV exposure, the matrix 600 may account for the intersection of these factors in another dimension of the matrix that is not illustrated in FIG. 6.

Figure 7:
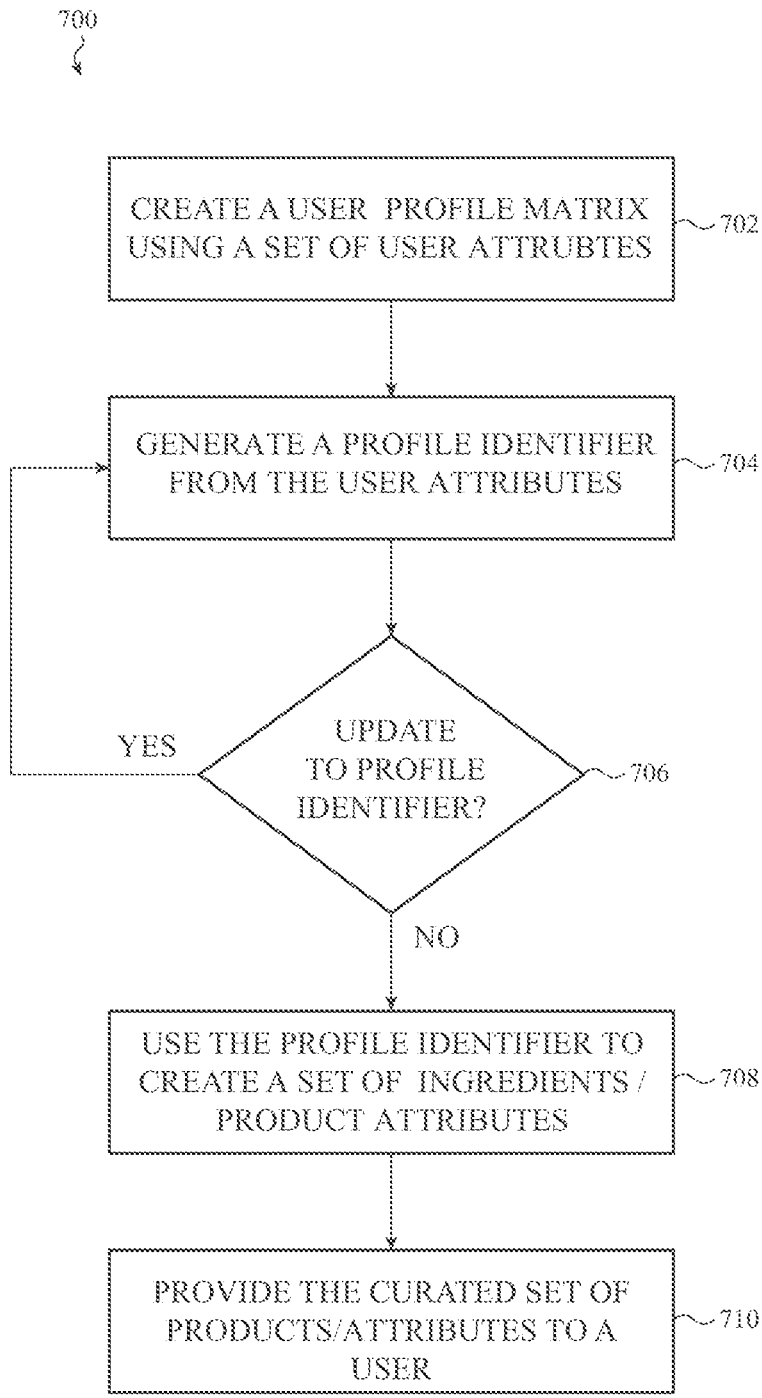
FIG. 7 illustrates an example method for providing a recommendation by leveraging a recommendation matrix, as described herein.

FIG. 7 illustrates an example method 700 for providing a skincare product recommendation. In some examples, the method 700 depicted in FIG. 7 may include additional processes not depicted in FIG. 7, or may exclude some of the processes in FIG. 7. Further, the processes of FIG. 7 are ordered for purposes of discussion, but may, in some examples, be performed in a different order. In the example of FIG. 7, the method 700 may include processes to correlate a one or more fingerprints related to the user to the user-specific attributes to generate a user's associated fingerprint(s). The user's associated fingerprint(s) may be used to select, prepare, and provide a curated product portfolio to the user.

In FIG. 7 and at 702, a user profile matrix may be created using a set of user-specific attributes. The user profile matrix may organize the user data, which may include user-specific attributes. The user-specific attributes may include skin-related factors and non-skin related factors. For skincare-related embodiments, skin-related factors may include skin concerns, skin type, allergies, skin issues, and so forth, while the non-skin related factors may be general information on the user. The non-skin related factors may include where the user lives, ethnicity, age, water intake, stress level, and so forth. The user profile matrix may include the user-specific attributes which may affect the skin of a user or which may exacerbate any existing skin conditions of the user.

At 704, a user's associated fingerprint(s) (e.g., demographic fingerprint, environmental fingerprint, preference fingerprint, concern/goal fingerprint, and so on) may be derived from the user profile matrix. The user's associated fingerprint(s) may be derived from mapping the one or more fingerprints related to the user to the user-specific attributes of the user profile matrix. In some examples, the user's associated fingerprint(s) may be a concatenated string of individual representative markers from the user profile matrix. The individual representative markers may represent unique intersections of the user-specific attributes.

At 706, updates to the user's associated fingerprint(s) are verified. In some examples, the user's associated fingerprint(s) includes an anticipated change. As discussed herein, the user's associated fingerprint(s) may be updated based on the anticipated change associated with the one or more fingerprints related to the user. In some examples, the one or more fingerprints related to the user may not change and the user's associated fingerprint(s) may be updated based on a trigger such as the month of the year. Because the user's associated fingerprint(s) may be updated, the curated product portfolio may also be altered and the updated products may be recommended to the user or provided to the user for purchase.

Anticipated changes may be built into the user's associated fingerprint(s) and may be triggered or signaled by various factors. In this example, there may not be a change or update to the one or more fingerprints related to the user even though the user's associated fingerprint(s) may be updated. In some examples, the anticipated change to the user's associated fingerprint(s) may be triggered by the time of year which may indicate a change in season and accordingly a temperature change depending on the geographic location of the user. The curated product portfolio may be updated based on the anticipated change or changes.

As indicated at 706, if it is confirmed that there are no updates to the user's associated fingerprint(s), then at 708, the user's associated fingerprint(s) may be used to create a curated set of skincare products. The user's associated fingerprint(s) may be used to select the appropriate and effective base ingredient and additives to address the skin issues and concerns of the user. At 710, the curated set of skincare products may be provided to the user for review and/or purchase.

Figure 8:
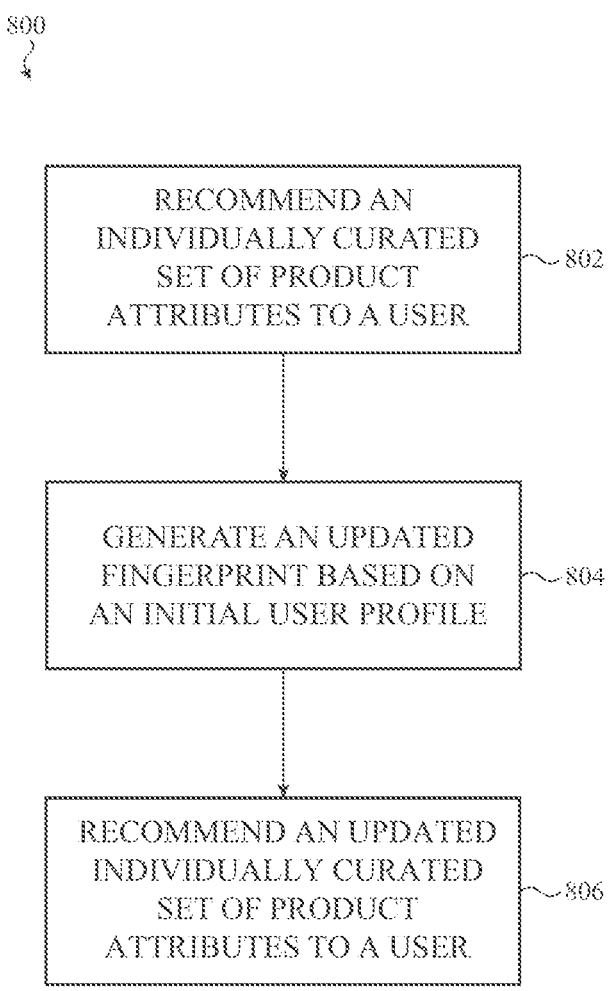
FIG. 8 illustrates an example method for providing and updating a recommendation provided by a recommendation system as described herein.

FIG. 8 illustrates an example method 800 for providing and updating a skincare product recommendation. In some examples, the method 800 depicted in FIG. 8 may include additional processes not depicted in FIG. 8, or may exclude some of the processes included in FIG. 8.

Further, the processes of FIG. 8 are ordered for purposes of discussion, but may, in some examples, be performed in a different order. In the example of FIG. 8, the method 800 may include processes to correlate a one or more fingerprints related to the user to the user-specific attributes to generate a user's associated fingerprint(s). The user's associated fingerprint(s) may be used to select, prepare, and provide a curated product portfolio to the user.

In FIG. 8 and at 802, an individually curated set of skincare products may be recommended to the user. The set of skincare products may be specifically formulated according to the initial skincare data entered by the user. The initial skincare data may be received by the skincare system and entered into the database and a user skincare profile may be created. The user skincare profile may be mapped to the user-specific attributes of the user profile matrix to derive a user's associated fingerprint(s).

In some examples, the individual elements of the user skincare profile may be matched to the corresponding user-specific attributes of the user profile matrix to derive a user's associated fingerprint(s). The user profile matrix may include user-specific attributes as discussed herein with respect to at least FIGS. 4-6. Each of the user-specific attributes may have an individual representative marker and these markers may be concatenated together to make up the user's associated fingerprint(s).

In some examples, the initial skincare data and the user's associated fingerprint(s) may include an anticipated change due to temperature or humidity changes for example. As discussed herein and at 804, an updated user's associated fingerprint(s) may be generated based on the anticipated change associated with the initial one or more fingerprints related to the user. In some examples, the one or more fingerprints related to the user may not change and the user's associated fingerprint(s) may be updated based on a trigger as discussed herein. Because the user's associated fingerprint(s) may be updated, the curated product portfolio may also be altered and the updated products may be recommended to the user or provided to the user for purchase as indicated at 806.

Figure 9:
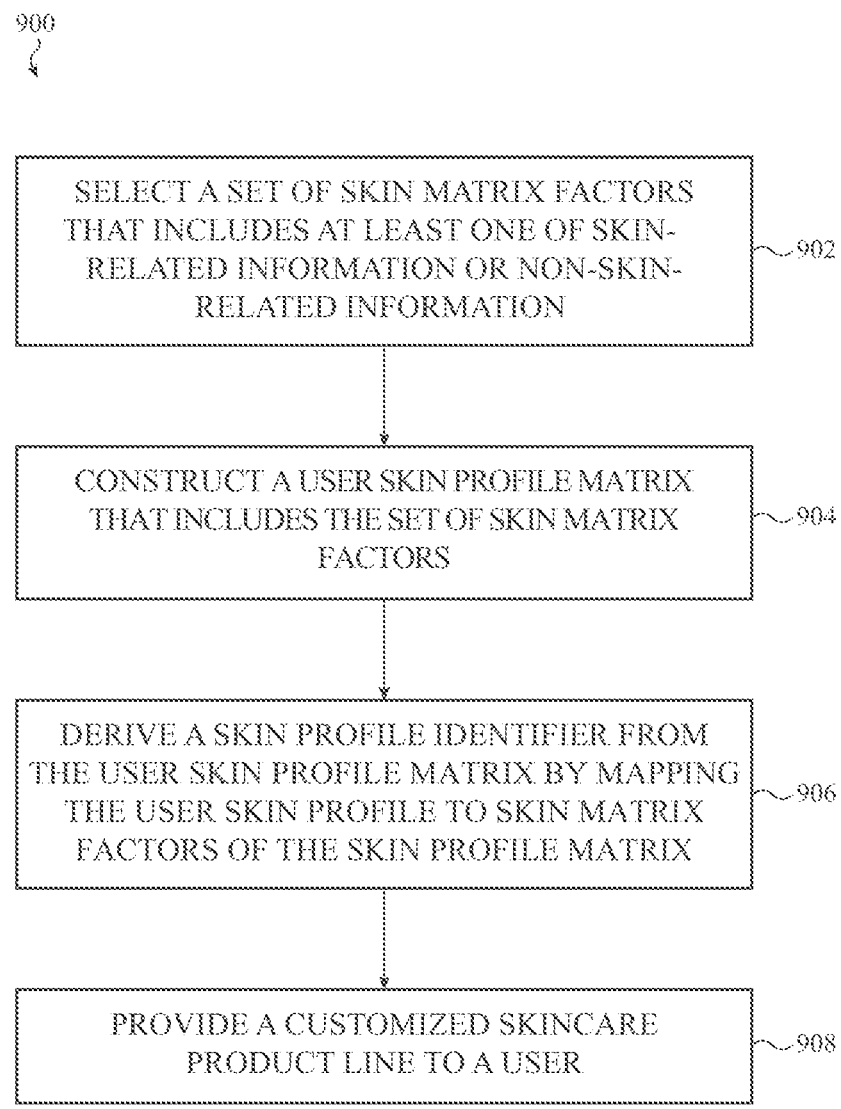
FIG. 9 illustrates an example method for providing a recommendation, as described herein.

FIG. 9 illustrates an example method 900 for providing a skincare product recommendation. In some examples, the method 900 depicted in FIG. 9 may include additional processes not depicted in FIG. 9, or may exclude some of the processes included in FIG. 9. Further, the processes of FIG. 9 are ordered for purposes of discussion, but may, in some examples, be performed in a different order. In the example of FIG. 9, the method 900 may include processes to correlate a one or more fingerprints related to the user to the user-specific attributes to generate a user's associated fingerprint(s). The user's associated fingerprint(s) may be used to select, prepare, and provide a curated product portfolio to the user.

In FIG. 9 and at 902, a set of user-specific attributes that includes at least one of a skin-related information or non-skin related information may be selected. The user-specific attributes may be selected based on whether the factor may affect a user's skin. These factors may include skin-related factors and non-skin related factors such as general user information.

At 904, a user profile matrix may be constructed that includes the set of user-specific attributes and at 906, a user's associated fingerprint(s) may be derived from the user profile matrix by mapping the one or more fingerprints related to the user to user-specific attributes of the user profile matrix. The user profile matrix may include intersections of various user-specific attributes. The user-specific attributes may include any relevant factor that may affect the skin and/or skin concerns of the user. In some examples, the user's associated fingerprint(s) may be a concatenated string of individual representative markers from the user profile matrix. The user's associated fingerprint(s) may then be used to select the base ingredients and the additives appropriate to address the skincare needs of the user and a customized skincare product line may be provided to the user at 908.

The described systems, process flows, and methods of the selection and recommendation of the curated product portfolios in FIGS. 1-9 have been for explanatory purposes. In alternative embodiments, the described embodiments may include a different combination or configuration of processes, or may perform additional or alternative functions. The process flows and configurations described herein may be used as part of a skincare system which may recommend a curated product portfolio, or in any other appropriate skincare system.

The foregoing description, for purposes of explanation, uses specific nomenclature to provide a thorough understanding of the described embodiments. However, it will be apparent to one skilled in the art, after reading this description, that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art, after reading this description, that many modifications and variations are possible in view of the above teachings.

The present disclosure recognizes that personal information data, including the skincare data acquired using the presently described technology, can be used to the benefit of users. In some examples, user-describing demographic data, preference data, and/or user personal care goal data is collected for providing users with feedback about their health or fitness levels, or the effectiveness of ingredients in the products or the products themselves. Further, other uses for personal information data, including skincare data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data, including skincare data. That is, the present disclosure contemplates that hardware and/or software elements can be provided to prevent or block access to such personal information data. In some examples, users can select to remove, disable, or restrict access to certain health-related applications collecting users' personal health or fitness data, skincare data, or general information on the user.

As used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

One may appreciate that although many embodiments are disclosed above, that the operations and steps presented with respect to methods and techniques described herein are meant as exemplary and accordingly are not exhaustive. One may further appreciate that alternate step order or fewer or additional operations may be required or desired for particular embodiments.

Although the disclosure above is described in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the some embodiments of the invention, whether or not such embodiments are described and whether or not such features are presented as being a part of a described embodiment. Thus, the breadth and scope of the present invention should not be limited by any of the above-described exemplary embodiments but is instead defined by the claims herein presented.

In addition, examples and description of instances of purpose-configured software, whether accessible via API as a request-response service, an event-driven service, or whether configured as a self-contained data processing service are understood as not exhaustive. In other words, a person of skill in the art may appreciate that the various functions and operations of a system such as described herein can be implemented in a number of suitable ways, developed leveraging any number of suitable libraries, frameworks, first or third-party APIs, local or remote databases (whether relational, NoSQL, or other architectures, or a combination thereof), programming languages, software design techniques (e.g., procedural, asynchronous, event-driven, and so on or any combination thereof), and so on. The various functions described herein can be implemented in the same manner (as one example, leveraging a common language and/or design), or in different ways. In many embodiments, functions of a system described herein are implemented as discrete microservices, which may be containerized or executed/instantiated leveraging a discrete virtual machine, that are only responsive to authenticated API requests from other microservices of the same system. Similarly, each microservice may be configured to provide data output and receive data input across an encrypted data channel. In some cases, each microservice may be configured to store its own data in a dedicated encrypted database; in others, microservices can store encrypted data in a common database; whether such data is stored in tables shared by multiple microservices or whether microservices may leverage independent and separate tables/schemas can vary from embodiment to embodiment. As a result of these described and other equivalent architectures, it may be appreciated that a system such as described herein can be implemented in a number of suitable ways. For simplicity of description, many embodiments that follow are described in reference an implementation in which discrete functions of the system are implemented as discrete microservices. It is appreciated that this is merely one possible implementation.

As described herein, the term "processor" refers to any software and/or hardware-implemented data processing device or circuit physically and/or structurally configured to instantiate one or more classes or objects that are purpose-configured to perform specific transformations of data including operations represented as code and/or instructions included in a program that can be stored within, and accessed from, a memory. This term is meant to encompass a single processor or processing unit, multiple processors, multiple processing units, analog or digital circuits, or other suitably configured computing element or combination of elements.

What is claimed is:

1. A method for maintaining user privacy and anonymizing user data when collecting information from a user of a recommendation system to generate a user-specific recommendation by the recommendation system, the method comprising:
at a computing system, receiving from a client device in communication with the computing system and operated by the user, information comprising:
a set of personal care objective identifiers, each personal care objective identifier corresponding to a respective one personal care objective reported by the user;

a set of demographic identifiers, each demographic identifier corresponding to a respective one demographic attribute reported by the user as describing the user; and a set of environmental identifiers, each environmental identifier corresponding to a respective one environmental attribute reported by the user and/or reported by the client device as describing a location occupied by the user;

generating, by the computing system, a first hash by providing as input to a one-way hashing function the set of demographic identifiers;

generating, by the computing system, a second hash by providing as input to the one-way hashing function the set of environmental identifiers;

generating, by the computing system, a third hash by providing as input to the one-way hashing function the set of personal care objective identifiers;

providing the first hash, the second hash, and the third hash as input to machine learning model having been trained against a structured dataset comprising:

a first dimension defined by a set of hashes based on demographic or environmental attributes extracted from and/or derived from public customer review data authored by anonymous review authors in respect of one or more consumer products;

a second dimension defined by a set of attributes of consumer products referenced in the public customer review data, the set of attributes extracted from at least one public resource;

a third dimension defined by a set of hashes based on personal care objectives extracted from and/or derived from the public customer review data; and normalized values corresponding to customer review author sentiment extracted and/or derived from of the public customer review data;

receiving, as output from the predictive model, a set of consumer product attributes that, if exhibited by a product used by the user, would be likely to elicit a positive sentiment review from the user;

instructing to be manufactured a custom product for the user, the custom product exhibiting the set of consumer product attributes received as output from the predictive model;

providing the custom product to the user; and updating the structured dataset and re-training the machine learning model in response to receiving input from the user regarding the custom product.

2. The method of claim 1, wherein the set of personal care identifiers corresponds to a personal care objective comprising one of
a skincare goal; or
a medical condition.

3. The method of claim 1, wherein the set of attributes corresponding to one or more consumer products comprises ingredients of one or more personal care products.

4. The method of claim 3, wherein the set of attributes corresponding to one or more consumer products comprises ingredients of one or more skincare products.

5. The method of claim 1, wherein the set of consumer product attributes is provided as output to the client device.

6. The method of claim 1, wherein the first hash is based on both the set of demographic attributes and the set of environmental attributes.

7. The method of claim 6, wherein the first hash is updated on a schedule to accommodate changes to the set of demographic identifiers or the set of environmental identifiers.

8. The method of claim 1, wherein at least one demographic identifiers of the set of demographic identifiers is determined from user input provided to the client device.

9. The method of claim 8, wherein the user input is provided in response to the client device rendering, in a graphical user interface of the client device, a questionnaire.

10. The method of claim 1, wherein at least one demographic attribute of the set of demographic is determined from a photograph or video of the user.

11. A method for maintaining user privacy and anonymity in a recommendation system configured to generate user-specific recommendations, the method comprising:

receiving, at a computing system, from a client device operated by a user, information comprising:
an identifier identifying a personal care objective; and
a hash generated by a one-way hashing function receiving as input a set of demographic and a set of environmental each set generated in response to input provided by the user to the client device;

providing, by the computing system, the hash and the identifier as input to a trained predictive model configured to provide as output a set of consumer product ingredients that if embodied in a consumer product used by the user to achieve the personal care objective would be likely to elicit a positive sentiment review from the user, the trained predictive model having been trained against a matrix data structure comprising:

a first dimension defined by a set of hashes based on demographic and environmental derived and/or extracted from customer review data generated from publicly-available consumer product reviews, each of which authored in respect of one or more consumer products;

a second dimension defined by a set of ingredients corresponding to each of the one or more consumer products, the set of ingredients associated with consumer product of the one or more consumer products determined from one or more third party databases;

a third dimension defined by a set of identifiers each identifier corresponding to a respective set of personal care objectives derived and/or extracted from each publicly-available consumer product reviews of the customer review data; and values corresponding to sentiment derived and/or extracted from each publicly-available consumer product reviews of the customer review data;

receiving as output of the trained predictive model, the a set of consumer product ingredient;

instructing, by the computing system, formulation of a user-specific custom product based on the set of consumer product ingredients; and providing the user-specific custom product to the user.

12. The method of claim 11, wherein the trained predictive model is further configured to provide as output a product attribute list comprising product that are likely to elicit a negative review from the user.

13. The method of claim 11, wherein the personal care objective relates to one of:
skincare; or
haircare.

14. The method of claim 11, wherein the hash is calculated by the client device.

15. The method of claim 11, wherein the data structure is stored in a database accessible to the computing system.

16. The method of claim 11, wherein the hash is recalculated on a schedule.

\* \* \* \* \*